United States Patent
Ketola et al.

(10) Patent No.: US 9,670,508 B2
(45) Date of Patent: Jun. 6, 2017

(54) BIOGAS PROCESS WITH NUTRIENT RECOVERY

(71) Applicant: Ductor Oy, Helsinki (FI)

(72) Inventors: Ari Ketola, Helsinki (FI); Kerttu Koskenniemi, Helsinki (FI); Minna Lahtinen, Espoo (FI); Jarkko Nummela, Helsinki (FI); Nina Virolainen, Helsinki (FI); Ilkka Virkajärvi, Espoo (FI)

(73) Assignee: DUCTOR OY, Helsinki (FI)

( * ) Notice: Subject to any disclaimer, the term of this patent is extended or adjusted under 35 U.S.C. 154(b) by 106 days.

(21) Appl. No.: 14/675,132

(22) Filed: Mar. 31, 2015

(65) Prior Publication Data

US 2015/0275234 A1 Oct. 1, 2015

Related U.S. Application Data

(60) Provisional application No. 61/973,577, filed on Apr. 1, 2014.

(51) Int. Cl.
   *C12P 5/02* (2006.01)
   *C12M 1/107* (2006.01)
   *C12P 23/00* (2006.01)

(52) U.S. Cl.
   CPC ............ *C12P 5/023* (2013.01); *C12M 21/04* (2013.01); *C12P 23/00* (2013.01); *Y02E 50/343* (2013.01)

(58) Field of Classification Search
   CPC ................................ C12P 5/023; Y02E 50/343
   (Continued)

(56) References Cited

U.S. PATENT DOCUMENTS

| 6,464,875 B1 | 10/2002 | Woodruff |
| 6,716,351 B2 | 4/2004 | Fassbender |

(Continued)

FOREIGN PATENT DOCUMENTS

| CN | 1308036 A | 8/2001 |
| CN | 102020508 A | 4/2011 |

(Continued)

OTHER PUBLICATIONS

International Preliminary Report on Patentability issued by the European Patent Office acting as the International Preliminary Examining Authority for International Application No. PCT/IB2015/052379 dated Apr. 5, 2016 (8 pages).

(Continued)

*Primary Examiner* — Michael Hobbs
(74) *Attorney, Agent, or Firm* — Robert P. Michal, Esq.; Carter, DeLuca, Farrell & Schmidt, LLP

(57) ABSTRACT

The invention is a method of two-phase anaerobic digestion where monitoring and adjusting the nitrogen status (carbon to nitrogen molar ratio, i.e. C/N molar ratio or total or ammoniacal nitrogen content) enables maintaining optimum conditions during the process. The method improves the use of a variety of feedstock materials or facilitates monodigestion of one feedstock. Especially the introduction of nitrogen rich feedstock materials in the process is amended. A community of hydrolyzing and acidogenic microorganisms in the first phase digester performs ammonification i.e. release of organic nitrogen as ammonia. Nitrogen and phosphorus are removed and recovered from the digestate which then undergoes biogasification in the second phase of the process. Reject water from biogasification can be recycled within the process.

8 Claims, 4 Drawing Sheets

(58) Field of Classification Search
USPC .......................................................... 435/167
See application file for complete search history.

(56) References Cited

U.S. PATENT DOCUMENTS

| | | | |
|---|---|---|---|
| 6,776,816 B1 | 8/2004 | Ringelberg et al. | |
| 8,574,889 B1 | 11/2013 | Latvala et al. | |
| 8,691,551 B1 | 4/2014 | Lahtinen et al. | |
| 2009/0107913 A1* | 4/2009 | Johnson .................. | C05F 5/008 210/604 |
| 2011/0126455 A1 | 6/2011 | Shinohara | |
| 2011/0126457 A1 | 6/2011 | Shinohara | |
| 2014/0271438 A1 | 9/2014 | Oksanen et al. | |

FOREIGN PATENT DOCUMENTS

| | | |
|---|---|---|
| CN | 102112609 A | 6/2011 |
| DE | 10 2012 211 781 A1 | 1/2014 |
| DE | 10 2013 212 357 A1 | 1/2014 |
| EP | 1964828 B1 | 10/2008 |
| EP | 2039775 A2 | 3/2009 |
| JP | 6-191976 A | 7/1994 |
| JP | 2009279534 A | 12/2009 |
| JP | 2011240254 A | 12/2011 |
| WO | 0242227 A1 | 5/2002 |
| WO | WO 2006/119052 A2 | 11/2006 |
| WO | 2010120173 A1 | 10/2010 |
| WO | 2011112736 A2 | 9/2011 |

OTHER PUBLICATIONS

Ward, et al., "Optimisation of the Anaerobic Digestion of Agricultural Resources," Bioresource Technology, vol. 99, No. 17, Nov. 1, 2008, p. 7928-7940.

Dioha et al., "Effect of Carbon to Nitrogen Ratio on Biogas Production," International Research Journal of Natural Sciences, vol. 1, No. 3, pp. 1-10, Sep. 2013.

Zeshan et al., "Effect of C/N Ratio and Ammonia-N Accumulation in a Pilot-Scale Thermophilic Dry Anaerobic Digester", Biosource Technology, vol. 113, Feb. 2012, pp. 294-302.

Resch et al., "Enhancement Options for The Utilisation of Nitrogen Rich Animal By-Products in Anaerobic Digestion", Biosource Technology, vol. 102, No. 3, Feb. 2011, pp. 2503-2510.

Wang et al., "Optimizing Feeding Composition and Carbon-Nitrogen Ratios for Improved Methane Yield During Anaerobic Co-Digestion of Dairy, Chicken Manure and Wheat Straw", Biosource Technology, vol. 120, Jun. 2012, pp. 78-83.

Kayhanian, "Ammonia Inhibition in High-Solids Biogasification: An Overview and Practical Solutions", Environmental Technology, vol. 20, No. 4, Apr. 1, 1999, pp. 355-365.

Gelegenis et al., "Optimization of Biogas Production from Olive-Oil Mill Wastewater, by Codigesting with Diluted Poultry-Manure", Science Directed—Applied Energy, vol. 84, No. 6, Apr. 6, 2007, pp. 646-663.

International Search Report, International Application No. PCT/IB2015/052379, dated Jul. 24, 2015 (3 pages).

Written Opinion of the International Searching Authority, International Application No. PCT/IB2015/052379, dated Jul. 24, 2015 (7 pages).

Attwood et al. 1998 "Ammonia-Hyperproducing Bacteria from New Zealand Ruminants", Applied and Environmental Microbiology, May 1998, p. 1796-1804 (10 pages).

David L. Balkwill, et al., "Equivalence of Microbial Biomass Measures Based on Membrane Lipid and Cell Wall Components, Adenosine Triphosphate, and Direct Counts in Subsurface Aquifer Sediments," Microbial Ecology, 1988, vol. 16, p. 73-84, (13 pages).

Frank R. Bengelsdorf, et al., "Stability of a biogas-producing bacterial, archaeal and fungal community degrading food residues," Federation of European Microbiological Societies, 2013, vol. 84, p. 201-212, (12 pages).

Bladen, H. A., M. P. Bryant, and R. N. Doetsch. 1961. A study of bacterial species from the rumen which produce ammonia from protein hydrolysate. Appl. Microbiol. 9: 175-180 (6 pages).

Chen, G., and J. B. Russell. 1988. Fermentation of peptides and amino acids by a monensin-sensitive ruminal *Peptostreptococcus*. Appl. Environ. Microbiol. 54:2742-2749 (8 pages).

Chen, G.J., Russell, J.B. 1989. More monensin-sensitive, ammonia-producing bacteria from the rumen. *Appl. Environ. Microbiol.* 55, 1052-1057.

Chourey, K.; Jansson, J.; VerBerkmoes, N.; Shah, M.; Chavarria, K. L.; Tom, L. M.; Brodie, E. L.; Hettich, R. L. 2010. Direct cellular lysis/protein extraction protocol for soil metaproteomics. Journal of Proteome Research 9: 6615-6622 (8 pages).

Communication of Acceptance issued by the Finnish Patent Office in connection with Finnish Application No. 20125661 dated Jul. 11, 2013 (3 pages).

PCT International Search Report and Written Opinion mailed Jun. 30, 2014 and issued by International Searching Authority of European Patent Office in PCT International Application No. PCT/IB2014/059539 (17 pages).

Dott et al., "Comparison of autochthonous bacteria and commercially available cultures with respect to their effectivenesss in fuel oil degradation," Journal of Industrial Microbiology, vol. 4, No. 5, 1989, pp. 365-374, XP008169913.

Dowd, S.E., et al., "Polymicrobial Nature of Chronic Diabetic Foot Ulcer Biofilm Infections Determined Using Bacterial Tag Encoded FLX Amplicon Pyrosequencing (bTEFAP)," PloS One, Oct. 2008, Vo. 3(10):e3326, (7 pages).

Dowd, S.E., Sun, Y., Secor, P.R., Rhoads, D.D., Wolcott, B.M., James, G.A., Wolcott, R.D. 2008b. Survey of bacterial diversity in chronic wounds using Pyrosequencing, DGGE, and full ribosome shotgun sequencing. *BMC Microbiology* 8: 43.

Ductor Corp., "Ductor Corp. gets R&D funding for research and development to biologically produce ammonia and phosphates—World's first 100% organic method to replace chemical fertilizers and secure global food supply," Internet citation, Jan. 28, 2013, XP002725135 (1 page).

EC. 2009. Regulation (EC) No. 1069/2009 of the European Parliament and of the Council of Oct. 21, 2009 laying down health rules as regards animal by-products and derived products not intended for human consumption and repealing Regulation (EC) No. 1774/2002 (Animal by-products Regulation). *Off. J. Eur. Union* L300: 1-33.

Eschenlauer, S. C. P., N. McKain, N. D. Walker, N. R. McEwan, C. J. Newbold, and R. J. Wallace. 2002. Ammonia production by rumen microorganisms and enumeration, isolation, and characterization of bacteria capable of growth on peptides and amino acids from the sheep rumen. Appl. Environ. Microbiol. 68:4925-4931 (8 pages).

EU. 2011. Commission regulation (EU) No. 142/2011 of Feb. 25, 2011 implementing Regulation (EC) No. 1069/2009 of the European Parliament and of the Council laying down health rules as regards animal by-products and derived products not intended for human consumption and implementing Council Directive 97/78/EC as regards certain samples and items exempt from veterinary checks at the border under that Directive. *Off J. Eur. Union* L54: 1-354.

Kjell Magne Fagerbakke, et al., "Content of carbon, nitrogen, oxygen, sulfur and phosphorus in native aquatic and cultured bacteria," Aquatic Microbial Ecology, Mar. 14, 1996, vol. 10, p. 15-27, (13 pages)

Michael D. Flythe, et al., "Fermentation acids inhibit amino acid deamination by Clostridium sporogenes MD1 via a mechanism involving a decline in intracellular glutamate rather than protonmotive force," Microbiology, 2006, vol. 152, p. 2619-2624, (6 pages).

Fouts, D.E., Szpakowski, S., Purushe, J., Torralba, M., Waterman, R.C., MacNeil, M.D., Alexander, L.J., Nelson, K.E. 2012. Next generation sequencing to define prokaryotic and fungal diversity in the bovine rumen. *PLoS One* 7(11): e48289.

Gowariker, V., Krishnamurthy V. N., Gowariker S., Dhanorkar, M., Kalyani P. 2009. Ammonification. In: The Fertilizer Encyclopedia. p. 41-41 John Wiley & Sons, Inc., Hoboken, New Jersey (4 pages).

(56) References Cited

OTHER PUBLICATIONS

Guerrero, L., et al., "Anaerobic hydrolysis and acidogenesis of wastewaters from food industries with high content of organic solids and protein," Water Research, Oct. 1999, vol. 33, Nr. 15, p. 3281-3290 (3 pages).
Guštin S., Marinšek-Logar R. 2011. Effect of pH, temperature and air flow rate on the continuous ammonia stripping of the anaerobic digestion effluent, Process Safety and Environmental Protection 89: 61-66 (6 pages).
Hernandez-Eugenio et al., "*Sporanaerobacter acetigenes* gen. nov., sp. nov., a novel acetogenic, facultatively sulfur-reducing bacterium," International Journal of Systematic and Evolutionary microbiology, vol. 52, No. 4, Jul. 1, 2002, pp. 1217-1223 XP055123612.
Hungate R.E. 1969. A Roll Tube Method For Cultivation of Strict Anaerobes in Methods of Microbiology, vol. 111 p. 117-132, Academic Press, London (9 pages).
Napon Keanoi, et al., "The effect of natural water with cow dung and agricultural waste ratio on biogas production from anaerobic co-digestion," American Journal of Environmental Science, 2013, vol. 6, p. 529-536, (8 pages).
Krause, D.O., Russell, J.B. 1996. An rRNA approach for assessing the role of obligate amino acid-fermenting bacteria in ruminal amino acid deamination. *Appl. Environ. Microbiol.* 62, 815-821.
Nakashimada et al, "Ammonia-Methane two-stage anaerobic digestion of dehydrated waste-activated sludge," Applied Microbiology and Biotechnology, vol. 79. No. 6, May 20, 2008, pp. 1061-1069, XP019623654.
Navarrete del Toro MA, Garda-Carrěno FL. 2002. Evaluation of the Progress of Protein Hydrolysis. Current Protocols in Food Analytical Chemistry B2.2.1-B2.2.14 (14 pages).
Nelson, N.O., Mikkelsen, R.L. & Hesterberg, D. L. 2003. Struvite precipitation in anaerobic swine lagoon liquid: effect of pH and Mg:P ratio and determination of rate constant. Bioresource Technology 89: 229-236 (8 pages).
Opinion on Patentability dated Mar. 19, 2013 issued by the National Board of Patents and Registration of Finland in Finnish Patent Application No. 20125661 (5 pages).
Paster, B. J., J. B. Russell, C. M. J. Yang, J. M. Chow, C. R. Woese, and R. Tanner. 1993. Phylogeny of the ammonia-producing ruminal bacteria *Peptostreptococcus anaerobius, Clostridium sticklandii* and *Clostridium aminophilum* sp. nov. Int. J. Syst. Bacteriol. 43: 107-110 (4 pages).
Ian R. Ramsay, et al., "Protein degradation during anaerobic wastewater treatment: derivation of Stoichiometry," Biodegradation, 2001, vol. 12, p. 247-257, (11 pages).
Christoph Resch, et al., "Enhancement options for the utilisation of nitrogen rich animal by-products in anaerobic digestion," Bioresource Technology, 2011, vol. 102, p. 2503-2510, (8 pages) XP027582877.
Russell, J. B., H. J. Strobel, and G. Chen. 1988. Enrichment and isolation of a ruminal bacterium with a very high specific activity of ammonia production. Appl. Environ. Microbiol. 54:872-877 (6 pages).
Rychlik, J. L., and J. B. Russell. 2000. Mathematical estimations of hyper-ammonia producing ruminal bacteria and evidence for bacterial antagonism that decreases ruminal ammonia production. FEMS Microbial. Ecol. 32: 121-128 (8 pages).
Schulze-Rettmer, R., von Fircks, R. & Simbach, B. 2001. MAP precipitation—pilot plant investigation in Germany. Environmental Technology (10 pages).
Search Report dated Mar. 19, 2013 issued by the National Board of Patents and Registration of Finland in Finnish Patent Application No. 20125661 (2 pages).
Smil, V. 2001. Evolution of Ammonia Synthesis. In: Enriching the Earth. Fritz Haber, Carl Bosch, and the Transformation of World Food Production. p. 109-132. MIT Press. Cambridge (USA), London ISBN 0-262-19449-X (15 pages).
Barros Soares et al., "Influence of some commercial proteases and enzymatic associations on the hydrolytic solubilization of deboned poultry meat proteins". Food Science and Technology International, (Aug. 2000), vol. 6, No. 4, pp. 301-306.
Carina Sundberg, et al., "454 pyrosequencing analyses of bacterial and archaeal richness in 21 full-scale biogas digesters," Federation of European Microbiological Societies, 2013, vol. 85, p. 612-626, (15 pages).
US Geological Survey. 2012. Nitrogen (fixed)—ammonia. US Department of Interior, Mineral Commodity Summaries, p. 112-113. US Department of Interior, US Geological Survey (8 pages).
Vince AJ, Burridge SM. 1980. Ammonia production by intestinal bacteria: the effects of lactose, lactulose and glucose. J Med Microbiol 13: 177-91 (15 pages).
Whitehead TR, Cotta MA. 2004. Isolation and identification of hyper-ammonia producing bacteria from swine manure storage pits. Curr Microbiol 48: 20-26 (7 pages).
Randall D Wolcott, et al., "Evaluation of the bacterial diversity among and within individual venous leg ulcers using bacterial tag-encoded FLX and Titanium amplicon pyrosequencing and metagenomic approaches," BMC Microbiology, Oct. 27, 2009, vol. 9, p. 226 (11 pages).
Yabu, Hironori; et al; "Thermophilic two-stage dry anaerobic digestion of model garbage with ammonia stripping" Journal of Bioscience and Bioengineering, 111,312-319,2011.
Yadvika, et al., "Enhancement of biogas production from solid substrates using different techniques—a review," Bioresource Technology, 2004, vol. 95, p. 1-10, (10 pages).
Zeng et al., "Ammonia recovery from anaerobically digested cattle manure by steam stripping" Water Science & Technology, vol. 54, No. 8, Aug. 1, 2006, p. 137-145, XP055123390.
Chen Zhang, et al., "Inhibitory effects of ammonia on methanogen mcrA transcripts in anaerobic digester sludge," Federation of European Microbiological Societies, 2014, vol. 87, p. 368-377, (10 pages).

\* cited by examiner

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Universal 16S RNA Bacteria Primer
<220> FEATURE:
<221> NAME/KEY: misc_feature
<222> LOCATION: (11)..(11)
<223> OTHER INFORMATION: n is a, c, g, or t

<400> SEQUENCE: 1
gagtttgatc ntggctcag                                    19

<210> SEQ ID NO 2
<211> LENGTH: 18
<212> TYPE: DNA
<213> ORGANISM: Artificial
<220> FEATURE:
<223> OTHER INFORMATION: Universal 16S RNA Bacteria Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: k is t or g

<400> SEQUENCE: 2
gtnttacngc ggckgctg                                     18

BIOGAS PROCESS WITH NUTRIENT RECOVERY

FIELD OF THE INVENTION

This invention relates to an integrated process for optimizing the production of biogas by two-phase anaerobic digestion (AD) of feedstock, i.e., biomass or organic material. The integrated process of the invention particularly relates to determining the nitrogen status (carbon to nitrogen molar ratio, i.e. C/N molar ratio or total or ammoniacal nitrogen content) in the feedstock and at various steps of the process. More particularly, the invention provides utilization of nitrogen status control for optimization of the AD process and for introducing a variety of different feedstock materials into the process. The method of the invention employs ammonifying microbes for nitrogen mineralization during the first phase of AD, and a nitrogen and phosphate removal and recovery step before starting the second phase of AD to produce biogas. In addition, the method of the invention facilitates recirculation of biogasification reject water into the process.

BACKGROUND OF THE INVENTION

Anaerobic digestion of biomass occurs in four stages; (1) hydrolysis, (2) acidogenesis, (3) acetogenesis and (4) methanogenesis. During hydrolysis, polymeric organic molecules are broken down to smaller units such as oligomers, dimers and monomers. Depending on starting material, these smaller units are sugars, amino acids or fatty acids. Acidogenesis then converts these molecules to short-chain carboxylic acids, ketones, alcohols, hydrogen and carbon dioxide. During acetogenesis the short-chain carboxylic acids and alcohols are converted to acetic acid, hydrogen and carbon dioxide, which then are converted to methane during methanogenesis. Different stages of anaerobic digestion are performed by distinct groups of microbes. Together these groups form a microbial consortium capable of synergistic digestion of biomass. The consortium consists of (a) hydrolytic microbes and acidogens, (b) acetogens, and (c) methanogens. Biogas produced as the result of anaerobic digestion is a mixture of methane (50-75%) and carbon dioxide (25-50%), as well as minor amounts of other components such as hydrogen sulfide, nitrogen, hydrogen, moisture, oxygen, ammonia and siloxanes.

A significant part of the nitrogen in organic material is present in amino acids which make up the protein fraction of the organic matter of the feedstock material or biomass. In the process of anaerobic digestion, the proteolytic and protein fermenting bacteria are mainly members of the genus *Clostridium* (Ramsay & Pullammanappallil, 2001). It has previously been reported in co-owned U.S. published patent application US2014/0271438 A1 and co-owned U.S. Pat. No. 8,691,551, that the mixed bacterial population S1 (deposited under the terms of the Budapest Treaty as CBS accession No. 136063) is highly active in degrading nitrogenous compounds in various organic materials through anaerobic hydrolysis and acidogenesis. Simultaneously, the microbial activity releases organic nitrogen as inorganic ammonia/ammonium in a process called ammonification or nitrogen mineralization.

Other sources of nitrogen in organic materials commonly used as feedstock material are urea, uric acid and ammonia present in, e.g. animal urine and manure. In addition, materials such as wastewater sludge can contain a high amount of nitrogen in compounds such as nucleic acids. Plant biomass and silage can be rich in nitrates, among other forms of nitrogen. The feedstock materials typically used in the process of this invention include, but are not limited to, animal by-products, fish by-products, slaughterhouse waste, organic fraction(s) of municipal solid waste, energy crops, food waste, sewage sludge, food industry by-products, and crop culturing by-products.

"Feedstock" or "feedstock material," as used herein is defined as raw material supplied to a processing plant. Biogas production from nitrogen rich feedstock materials, e.g., organic waste materials, is accompanied by the release of proteinacious nitrogen as ammonia. High ammonia concentrations inhibit the activity of microbes involved in anaerobic digestion, and this in turn leads to an accumulation of short chain carboxylic acids i.e. volatile fatty acids (VFA). A recent study has shown that such high ammonia concentrations cause a decrease in expression of methyl-coenzyme M reductase, the enzyme catalyzing the terminal methane-forming reaction of methanogenesis (Zhang et al. 2014). This leads to a decreased use of acetic acid by acetoclastic methanogens, and a subsequent pH decline caused by the accumulation of VFA. This change in conditions can in turn lead to cessation of protein hydrolysis, acidogenesis and ammonification, as demonstrated in culture with *Clostridium sporogenes* MD1, where an influx of anionic VFA caused efflux of intracellular glutamate, the universal carrier of amino groups in deamination and transamination reactions of amino acid metabolism (Flythe & Russell 2006). In addition, end product inhibition caused by high ammonia levels is thought to slow down metabolic processes that produce ammonia. Therefore, excess ammonia affects the anaerobic digestion process on many levels, decreasing both the efficiency of its own production as well as biogas production.

Controlling the carbon to nitrogen (C/N) molar ratio of feedstock can reduce the ammonia load during AD. C/N molar ratio expresses the number of carbon atoms present per each nitrogen atom. C/N ratio can also be calculated and expressed as the ratio of masses of carbon and nitrogen. C/N molar ratio can be derived from C/N mass ratio by multiplication by 1.17, i.e. the C/N molar ratio is 17% higher than C/N mass ratio. The calculation is based on the differences in molar mass of carbon and nitrogen atoms. Alternative ways of presenting carbon or nitrogen for C/N ratio calculation include chemical oxygen demand (COD) or total organic carbon (TOC) to represent the amount of carbon and total Kjeldahl nitrogen (TKN) or total nitrogen (signifies total elemental nitrogen or the sum of nitrate $NO_3^-$, nitrite $NO_2^-$, organic nitrogen and ammonia nitrogen, depending on determination method) to represent the amount of nitrogen.

In biogas production, a high C/N ratio i.e. lack of nitrogen, leads to the inefficient utilization of carbon due to a lowered amount of microbial biomass, whereas a low C/N ratio, i.e. a surplus of nitrogen, can cause ammonia inhibition of methanogenesis. An optimal C/N ratio can be generated through the co-digestion of nitrogen rich and nitrogen poor feedstock materials. However, for example, in the biogasification of nitrogen rich animal slaughter by-products, an increase of COD through co-digestion with carbon rich feedstock did not enhance methane production from the nitrogen rich feedstock (Resch et al. 2011). Two-phase AD for nitrogen rich feedstock materials, with accompanying nitrogen recovery by stripping, has been suggested for lowering ammonia concentration during biogasification (U.S. Pat. No. 6,716,351 B2). The '351 patent process, however, limits its scope to nitrogen rich feedstock materials.

Two-phase AD with separate acidogenic and methanogenic phases has been described previously in the patent literature. For example, U.S. Pat. No. 4,022,665 discloses a two-phase system where the recycling of biogasification reject water back to the first phase, hydrolysis/acidogenesis, is presented as an option. Patent documents U.S. Pat. No. 7,309,435 B2, EP 1,181,252 B1 and EP 2,220,004 B1 describe two-phase systems where control of oxidation-reduction potential, VFA concentration, or pH, respectively, is used to enhance process efficiency. Patent document U.S. Pat. No. 8,642,304 B2 discloses a two-phase system where control of VFA concentration between two methanogenic reactors improves digestion. None of these documents identify and describe a microbial community for performing hydrolysis and acidogenesis, describe nutrient recovery, are concerned with feedstock composition or the possibility of co-digestion or monodigestion, or employing nitrogen status control as a method for enhancing biogas production.

Ammonia removal methods other than stripping have also been used in AD. Patent application EP 2,039,775 A2 discloses a two-phase system where ammonia fermentation performed with a single, or a mix of bacterial strains, is associated with ammonia removal as gaseous ammonia through agitation of the fermented material. Ammonia is either lost to the atmosphere or recovered as such for hydrogen production, but not recovered in a form suitable for fertilizer use. In addition, the conditions used, a mildly alkaline pH of 8-8.5 and a temperature of 55-65° C. do not favor volatilization of ammonia. Patent application EP 2,614,890 A1 describes a one-phase process where ammonia removal is based on ion exchange. The method requires chemicals for regeneration of the ion exchange resin and a careful removal of solid matter from the digestate prior to application to the resin.

Patent application WO 2013038216 A1 discloses a one-phase process where a characterized microbial community is used for AD of high-protein substrates. The community is, however very different from S1, consisting by up to 50% of bacteria of the Pseudomonales order, and also methanogenic archaea that are absent from S1.

Patent application EP 2,578,558 A1 discloses nitrogen recovery from AD by stripping that is performed by recycling the produced biogas. An inorganic ammonium salt fertilizer and a mixed organic fertilizer are produced as a result. No elevated pH is used during stripping, which may cause inefficient stripping of ammonia and lead to ammonia inhibition during AD.

Patent U.S. Pat. No. 8,613,894 B2 describes methods and systems for nutrient recovery from anaerobic digester effluent with different heating and aeration systems. In this process dissolved gases such as carbon dioxide, methane and ammonia are removed after AD with the aid of elevated temperature and aeration during 12-36 hours. The described process is time-consuming and will only remove ammonia to some extent.

Patent EP 0,970,922 B1 discloses a method for removal of inhibitory substances such as ammonia from biogas reactor by membrane separation of liquid and solid components. The downside of this method is that VFA are also washed out of the reactor along with ammonia, reducing the biogas yield.

Patent EP 1,320,388 B1 discloses a process for nutrient recovery from one-phase or two-phase AD through solid-liquid separation and ammonia stripping. Also reject water is recirculated within the process. The process does not characterize the microbial community performing conversion of organic nitrogen to inorganic nitrogen, and does not utilize nitrogen status control C/N ratio for providing optimal conditions for AD.

SUMMARY OF THE INVENTION

There is a long-standing need in the art for a process that provides a comprehensive solution to the above problems. Broadly, the inventive process can be conducted by fermenting feedstock in either a first reactor (for ammonification) and in a second reactor (for biogas production) or only in the second reactor, depending on whether the nitrogen content of the feedstock and reactor content is within an optimal range. The process of the invention provides flexibility at the feedstock interface, so that a one or more types of feedstock materials may be processed without an extended acclimatization period.

Thus, in one embodiment, the invention provides a process for optimizing production of biogas from one or more feedstock materials, which biogas production is conducted in at least a second reactor, the process including, (a) determining total elemental nitrogen (N) content in volatile solids (VS) or a carbon to nitrogen (C/N) molar ratio of the one or more feedstock materials, and (b) determining total elemental nitrogen content or total ammoniacal nitrogen content or C/N molar ratio of the contents of the second reactor, wherein the feedstock material is nitrogen rich when the C/N molar ratio of the feedstock material is below 15, or the total elemental nitrogen content in VS of the feedstock material is above 40 grams N per kilogram VS, wherein the feedstock material is carbon rich when the C/N molar ratio of the feedstock material is above 15, or the total elemental nitrogen content in volatile solids of the feedstock material is below 40 grams N per kilogram of VS, wherein the nitrogen status in the second reactor is optimal when the C/N molar ratio in reactor contents is between 5.0 and 12, or the amount of total ammoniacal nitrogen in reactor contents is between 0.1 and 2.5 grams per liter, or the amount of total elemental nitrogen in reactor contents is between 0.3 and 2.8 grams per liter, (c) when the nitrogen status determination in step (a) or step (b) indicates that the feedstock is nitrogen rich, or that the second reactor has a below optimum C/N molar ratio or an above optimum content of total ammoniacal or elemental nitrogen, treating the nitrogen rich feedstock in a first reactor with at least one ammonifying microbial species to produce an ammonia digestate, wherein an ammonia digestate is a digestate originating from the first reactor where the feedstock has been ammonified until preferably more than 50% of the total elemental nitrogen in the feedstock is converted to ammonia, (d) delivering the ammonia digestate from the first reactor to a nitrogen removal system, (e) treating the ammonia digestate in the nitrogen removal system to produce an ammonia-reduced digestate, wherein an ammonia-reduced digestate is an ammonia digestate that has passed through the nitrogen removal system to achieve removal of at least 80% of ammonia nitrogen, (f) delivering the ammonia-reduced digestate from the nitrogen removal system to the second reactor;

(g) when the nitrogen status determination in step (a) indicates that the feedstock is carbon rich, delivering carbon rich feedstock directly to the second reactor;

(h) when the nitrogen status determination in step (b) indicates that the second reactor has an above optimum C/N molar ratio or a below optimum content of total ammoniacal or elemental nitrogen, delivering nitrogen rich feedstock directly to the second reactor, the process further comprising (i) producing biogas from the delivered feedstock with at least one methanogenic microbial species in the second reactor, and (j) determining nitrogen status of the ammonia-reduced digestate after nitrogen removal and controlling efficiency of the nitrogen removal system and flow of ammonia-reduced digestate into the second reactor.

The at least one ammonifying microbial species is, in certain embodiments, a mixed microbial population or microbial community. The at least one methanogenic microbial species is, in certain embodiments, a microbial community. In certain aspects of the inventive process, the ammonifying mixed microbial population is S1, the mixed bacterial population that is deposited under CBS accession no. 136063.

Further, when the C/N molar ratio in the contents of the second reactor is above the optimum range, or the content of total elemental or ammoniacal nitrogen in the contents of the second reactor is below the optimum range, nitrogen is delivered to the second reactor by performing one or more of the following steps:

(i) adding ammonia nitrogen to the second reactor,
(ii) co-digesting nitrogen rich and carbon rich feedstock in the second reactor,
(iii) delivering nitrogen rich feedstock directly to second reactor without performing ammonification or nitrogen removal,
(iv) increasing the concentration of total ammoniacal nitrogen or total elemental nitrogen in the ammonia-reduced digestate through controlling nitrogen removal system efficiency and controlling flow of ammonia-reduced digestate into the second reactor.

The inventive process also optionally includes a step of reducing the content of solids in the ammonia digestate before introducing it to the nitrogen removal process. The solids removed from the ammonia digestate are optionally transferred directly into the second reactor, or to a phosphorus recovery process, before transfer of the solids to the second reactor.

The inventive process also optionally includes separating digestate from the second reactor into a solid fraction with an increased solids content and a liquid fraction with a reduced solids content; and recirculating the liquid fraction to the first or the second reactor.

The inventive process is conducted in a first and second, or second reactor, at a temperature range suitable for the selected substrate and microbes. Thus, the temperature in the first reactor and/or in the second reactor is in the mesophilic range, between 30° C. and 40° C., or is in the thermophilic range, between 45° C. and 60° C.

Preferably, when ammonia nitrogen is removed from the process as conducted in the first reactor, the recovered ammonia is in the form of ammonia water and/or as an ammonium salt.

Preferably, when phosphorus recovery is conducted as part of the inventive process, the phosphorus is recovered as either a phosphate solution or a salt precipitate. Optionally, phosphate solution is used as an absorber in nitrogen removal.

In a preferred embodiment, ammonification is performed in the first reactor as follows: firstly, a nitrogen rich feedstock comprising less than 60 grams of monosaccharides, oligosaccharides, starches or fermentable dietary fibers per kg of VS is delivered in the first reactor for preammonification, secondly, a nitrogen rich feedstock, the nitrogen rich feedstock comprising more than 60 grams of monosaccharides, oligosaccharides, starches or fermentable dietary fibers per kg of VS is delivered to the first reactor for continued ammonification with the preammonified feedstock.

Optionally, gas produced in the first reactor is directed to the second reactor to enhance biogas yield.

In a second embodiment, the invention provides a system for optimising production of biogas from a feedstock, which system includes:

a first reactor for treating feedstock to carry out ammonification to generate an ammonia digestate,
a system for nitrogen removal to generate an ammonia-reduced digestate from ammonia digestate,
a second reactor for producing biogas from the ammonia-reduced digestate,
means for delivering various types of feedstock to the first reactor separately,
means for delivering the ammonia digestate from the first reactor to the system for nitrogen removal
means for delivering the ammonia-reduced digestate from the system for nitrogen removal to the second reactor,
means for delivering feedstock or ammonia nitrogen directly to the second reactor.

In the system of the invention, the nitrogen status in the process is controlled by:

a first measurement system determining the total elemental nitrogen content in volatile solids or carbon to nitrogen molar ratio in feedstock,
a second measurement system determining the amount of total ammoniacal nitrogen, total elemental nitrogen or C/N molar ratio in the ammonia-reduced digestate after nitrogen removal,
a third measurement system determining the amount of total ammoniacal nitrogen,
total elemental nitrogen or C/N molar ratio in the contents of the second reactor,
means for controlling distribution of nitrogen rich feedstock, carbon rich feedstock or nitrogen rich feedstock comprising more than 60 grams of monosaccharides, oligosaccharides, starches or fermentable dietary fibers per kg of volatile solids into first or second reactor, for maintaining the amount of total ammoniacal nitrogen, total elemental nitrogen or C/N molar ratio in the second reactor within optimal range,
means for controlling efficiency of the nitrogen removal system and flow of the ammonified digestate stream into the second reactor, based on the measurement data from the second and third measurement system, for maintaining the amount of total ammoniacal nitrogen, total elemental nitrogen or C/N molar ratio in the second reactor within optimal range,
wherein the feedstock material is nitrogen rich when the C/N molar ratio of the feedstock material is below 15, or the total elemental nitrogen content in VS of the feedstock material is above 40 grams N per kilogram VS,
wherein the feedstock material is carbon rich when the C/N molar ratio of the feedstock material is above 15, or the total elemental nitrogen content in volatile solids of the feedstock material is below 40 grams N per kilogram of VS, wherein nitrogen status in the contents of the second reactor is optimal when the C/N molar ratio is between 5.0 and 12 or the amount of total ammoniacal nitrogen is between 0.1 and 2.5 grams per liter or the amount of total elemental nitrogen is between 0.3 and 2.8 grams per liter.

The system for nitrogen removal includes, for example, apparatus for air stripping of ammonia or ammonium produced during ammonification. The means for delivering feedstock to the first reactor, the means for delivering the ammonia digestate from the first reactor to the system for nitrogen removal, and the means for delivering the ammonia-reduced digestate from the system for nitrogen removal to the second reactor, and the means for delivering feedstock or ammonia nitrogen directly to the second reactor are contemplated to include suitable pumps, conduits, pipes, troughs, for transporting fluids and containers, and/or conveyers for moving solid or semi-solid materials.

DETAILED DESCRIPTION

Figure 1:
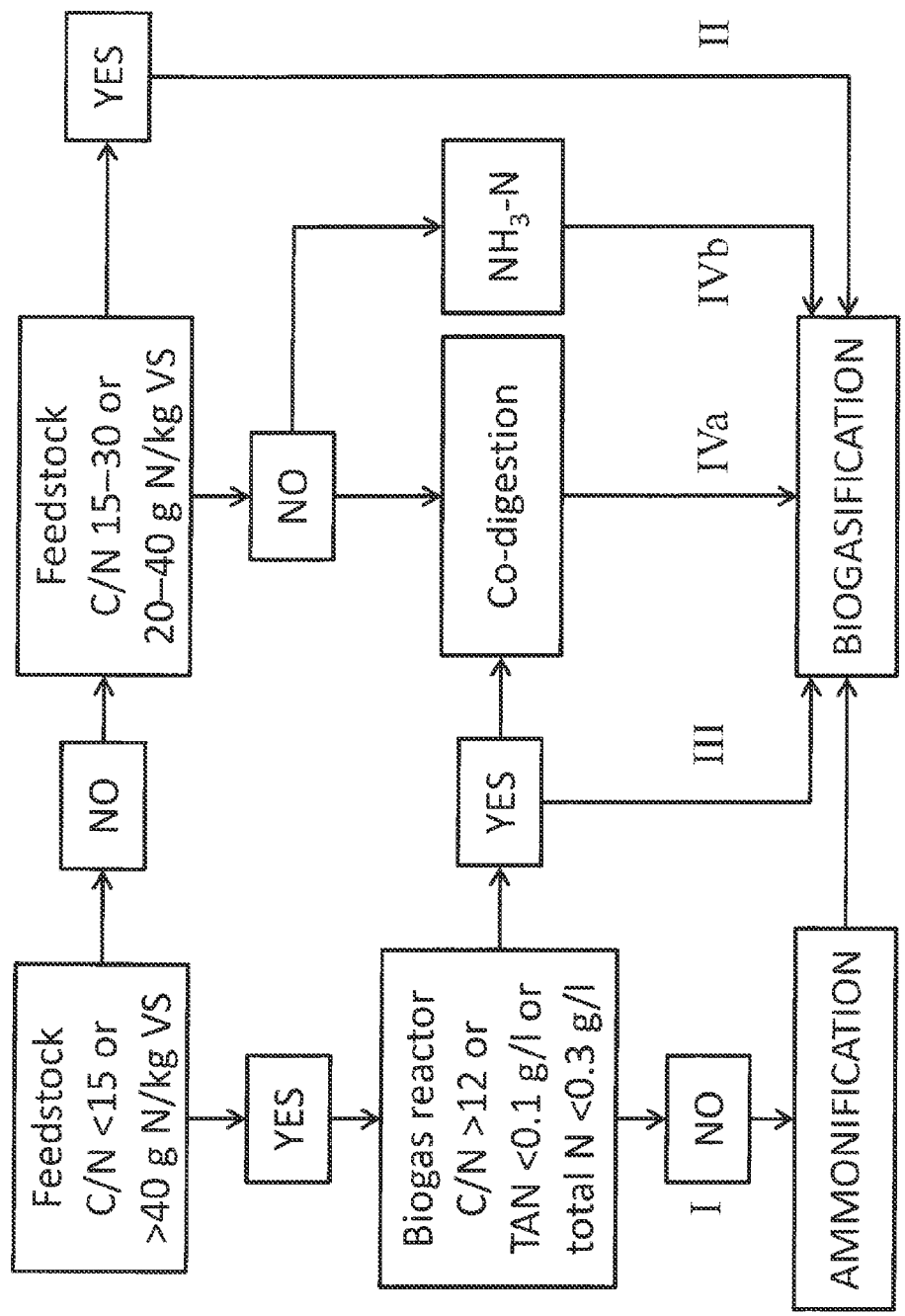
FIG. 1 is a scheme describing feedstock flow in a facility running the system of the present invention.

Accordingly, the invention provides an improved two-phase process for optimising the production of biogas from feedstock material, i.e., an organic material feedstock.

Here, a two-phase system for anaerobic digestion of organic material is provided. The first phase includes the hydrolysis and acidogenesis stages of anaerobic digestion performed in a first vessel containing an ammonifying microbial community. During this phase, the majority of organic nitrogen contained in the feedstock is released as ammonia. A nitrogen removal step follows ammonification. Any known method for nitrogen removal can be applied. After nitrogen removal, the material is used as biogas feedstock in the second phase of anaerobic digestion. To retain the methanogenic potential of the feedstock, it is important that as little as possible carbon is lost during the first phase. Therefore, the ammonification phase is performed anaerobically to minimize loss of carbon to the atmosphere as carbon dioxide. In addition, the nitrogen removal method should not consume or volatilize VFA produced during ammonification. After nitrogen removal the pH should be near neutral and ammonia concentration low enough to facilitate optimal conditions for biogasification. The flux of feedstock in the system is directed through observing and controlling the nitrogen status during different steps of the process.

The system offers several opportunities for increasing the productivity and profitability of the AD process: (1) a widened feedstock range; (2) more efficient and stable methane production due to a constant C/N ratio and total elemental or ammoniacal nitrogen concentration; (3) no extended acclimatization period required between different feedstock materials; (4) reduced wastewater treatment costs due to process water recirculation; (5) salable fertilizer components or products.

In order to more clearly appreciate the invention, the following terms are defined. The terms listed below, unless otherwise indicated, will be used and are intended to be defined as indicated. Definitions for other terms can occur throughout the specification.

It is intended that all singular terms also encompass the plural, active tense and past tense forms of a term, unless otherwise indicated.

The term "nitrogenous" is an adjective meaning containing the chemical element nitrogen.

The term "carbonaceous" is an adjective meaning containing the chemical element carbon.

The terms "feedstock" and "biomass" as employed herein refer to, for example, organic materials containing variable proportions of nitrogenous compounds, e.g., proteins, nucleic acids, urea and uric acid, and/or non-nitrogenous carbonaceous compounds such as, e.g., fats, celluloses, starches, sugars and lipids. Feedstock for the inventive process includes, for example, waste materials generated by industry, such as animal by-products, fish by-products, slaughterhouse waste, organic fraction of municipal solid waste, energy crops, food waste, sewage sludge, food industry by-products, and crop culturing by-products and the like.

The term "total solids" (TS) as employed herein is a measure of solid matter content of a material. It includes both soluble and insoluble solids (except easily volatilized compounds such as alcohols that may evaporate during the drying process). TS is the part that remains after drying the material sample at 103-105° C. for 20-22 hours or until constant weight.

The term "volatile solids" (VS) as employed herein refers to a measure of the organic content of a material. VS determination is performed to a material sample after TS determination, so the sample is dry before ignition. VS is the part that is volatilized (i.e. the weight lost) during ignition at 550° C. for 1-2 hours or until constant weight.

The terms "fermentation" or "fermenting" refer to an anaerobic microbial metabolic process where organic molecules serve as both electron donors and acceptors. It differs from respiration, where electrons derived from nutrient molecules are donated to oxygen (aerobic respiration) or other inorganic molecules/ions such as nitrate, sulfate, carbon dioxide or ferric iron (anaerobic respiration). In fermentation, nutrient molecules are reduced to small organic molecules such as volatile fatty acids and alcohols.

The terms "reactor", "bioreactor" or "digester" as used herein define a vessel used for anaerobic digestion, fermentation, biogasification, hydrolysis, acidogenesis or ammonification according to the invention, and these terms are used interchangeably herein unless otherwise specified.

The terms "biogasification" or "biogas production" as used herein define a microbial process of anaerobic digestion that principally produces a mixture of methane, carbon dioxide and other minor components (biogas) as a useful end product. The four stages of anaerobic digestion, hydrolysis, acidogenesis, acetogenesis and methanogenesis, lead to a breakdown of macromolecules contained in organic material to monomers and further to small soluble organic or inorganic compounds and the gaseous constituents of biogas.

The term, "reject water" as used herein is defined as the liquid phase of digestate from a biogasification reactor. Liquid is separated from the solid phase using methods such as flotation, flocculation, precipitation, filtration and sieving and devices such as a decanter centrifuge, a screw press, a roller press or a belt press.

The term "dilution water" as used herein is defined as water that is supplied to a reactor or a digester alone or with reject water to dilute the reactor or digester content to achieve a desired content of a desired measure such as TS, VS or TAN.

The term "ammonification" is defined herein as a microbial metabolic process during which nitrogen contained in organic molecules is converted to a form of inorganic nitrogen, ammonium/ammonia. In the process of this invention, ammonification occurs concurrently with hydrolysis and acidogenesis in the first reactor of the system in the presence of ammonifying microbes, whether a single species or strain of microbe, or a mixed microbial population or community of microbes.

The term "ammonifying microbial species" is defined herein as a species or strain of microbes useful for producing ammonia or ammonium during fermentation. Hydrolytic and acidogenic communities include bacterial genera such as *Bacteriocides, Clostridia, Bifdobacteria, Streptococci* and *Enterobacteriaceae*, some of them also present in the ammonifying mixed bacterial population S1 deposited under CBS accession No. 136063. In addition, single bacterial strains can perform the stages of hydrolysis, acidogenesis and ammonification, such as the hyper-ammonia producing bacteria *Peptostreptococcus anaerobius* C, *Clostridium sticklandii* SR and *Clostridium aminophilum* $F^T$, but typically cannot by themselves match the activity of a microbial consortium. An ammonifying community can arise from microbes contained in the feedstock material itself but as demonstrated in e.g. patent publication No. US20140271438, adding an inoculum of a microbial community specialized in breakdown and ammonification of nitrogenous biomolecules typically enhances and stabilizes process efficiency.

The S1 mixed bacterial population of US20140271438 was characterized by 16S pyrosequencing and data analysis, and consists of 98.7% of bacteria belonging to the order Clostridiales (TABLE 1). *Sporanaerobacter acetigenes* represents 75.9% of the total mixed bacterial population. Other common genera of the order Clostridiales present in S1 are *Clostridium* (15.5% of total population), *Caloramator* and *Tissierella*, and species *Mahella australiensis*. Bacteria belonging to other orders make up the remaining 1.3% of S1. S1 is typically able to release 60-80% of the nitrogen present in various organic materials, as ammonia, within 24-72 hours. S1 can tolerate high ammonia concentrations, showing activity at ≤16 g $NH_4^+$—N $L^{-1}$.

US20140271438 also described other ammonifying mixed bacterial populations, most notably a mixed bacterial population designated as C1. Bacterial community analysis of the mixed populations C1 and S1 was performed on DNA obtained by phenol-chloroform-isoamyl alcohol extraction from bacterial cultures where cells had been disrupted by bead beating. C1 population was created by mixing non-sterile meat-and-bone meal (MBM) manufactured by Findest Protein Oy, Finland with cold tap water in a proportion of 180 g MBM per liter of water. S1 population was created by mixing non-sterile MBM (SARIA Bio-Industries AG & Co. KG, Germany) with cold tap water in a proportion of 180 g MBM per liter of water. MBM was cultured without aeration at 50° C. until $NH_3$ concentration leveled out, and stationary growth phase was reached.

Before DNA extraction, populations had been cultured for four days at 50° C. by adding a 5% (volume/volume) inoculum of S1 or C1 in sterile MBM medium [180 g MBM per liter of water]. Bacterial 16S gene assay by tag-encoded FLX amplicon pyrosequencing (bTEFAP) and bacterial diversity data analysis were performed by the Research and Testing Lab (Lubbock, Tex., USA) as described by Dowd et al. 2008 and Wolcott et al. 2009. Primers 28F 'GAGTITT-GATCNTGGCTCAG' (SEQ ID NO: 1) and 519R 'GTNT-TACNGCGGCKGCTG' (SEQ ID NO: 2) were used for amplification of 16S variable regions V1-3 (wherein "N" is A, T/U, G or C and wherein "K" is T/U or G).

Bacterial diversity analysis revealed the presence of bacteria belonging to 15 different genera (TABLE 1). Of the total of 23 results, 16 were identified at the species level and 7 at the genus level. *Clostridium* spp. and *Sporanaerobacter acetigenes* are predominant in both populations.

To exemplify determination of similarity of S1 to other microbial communities, correlation coefficients were calculated from data presented in TABLE 1 using equation [1], where X and Y refer to the two matrices, C1 and S1, between which the correlation is calculated, x and y are single values within a matrix, and $\bar{x}$ and $\bar{y}$ are the means of all values within a matrix. Species not present in the population (empty cells in TABLE 1) were assigned a value 0.

$$Correl(X, Y) = \frac{\sum (x - \bar{x})(y - \bar{y})}{\sqrt{\sum (x - \bar{x})^2 \sum (y - \bar{y})^2}} \quad [1]$$

The term "substantially similar" with respect to a bacterial or microbial population as disclosed herein, means that a bacterial or microbial population has a correlation coefficient of at least 0.8 when compared to one or more of the bacterial populations defined by TABLE 1. Preferably, a substantially similar bacterial or microbial population has a correlation coefficient of at least 0.9, and more preferably, a substantially similar bacterial or microbial population has a correlation coefficient of at least 0.95 when compared to one or more of the bacterial populations defined by TABLE 1. The correlation coefficient between populations C1 and S1 was 0.9964.

TABLE 1

Bacterial diversity analysis results: genera and species in populations C1 and S1. The results are expressed as percentage of total population

| Species | C1 | S1 |
|---|---|---|
| *Bacillus* sp. | 0.530 | 0.398 |
| *Bacillus thermoamylovorans* | 0.106 | 0.085 |
| *Butyrivibrio fibrisolvens* | 0.021 | |
| *Caldicoprobacter oshimai* | 0.042 | 0.085 |
| *Caloramator* sp | 2.669 | 5.200 |
| *Clastridium botulinum* | 6.948 | 4.632 |
| *Clostridium cochlearium* | 6.439 | 8.497 |
| *Clostridium haemolyticum* | 0.064 | |
| *Clostridium oceanicum* | 0.064 | 0.057 |
| *Clostridium* sp | 0.487 | 0.568 |
| *Clostridium sporogenes* | 0.530 | 0.483 |
| *Clostridium ultunense* | 5.507 | 1.250 |
| *Garciella* sp | 0.085 | 0.028 |
| *Leptospira broomii* | 0.021 | |
| *Mahella australiensis* | 0.360 | 0.426 |
| *Microbacterium aurum* | 0.021 | |
| *Propionibacterium* sp | | 0.028 |
| *Pseudobutyrivibrio ruminis* | | 0.028 |
| *Sphingomonas mucosissima* | 0.021 | |
| *Sporanaerobacter acetigenes* | 74.26 | 75.87 |
| *Tepidanaerobacter* sp | 1.419 | 0.682 |

TABLE 1-continued

Bacterial diversity analysis results: genera and species in populations C1 and S1. The results are expressed as percentage of total population

| Species | C1 | S1 |
|---|---|---|
| Tissierella creatinophila | 0.021 | |
| Tissierella sp | 0.381 | 1.677 |

Thus, the degree of correlation between different mixed bacterial or microbial populations can be determined from the 16S DNA analysis, by calculating a correlation coefficient according to Formula 1.

The term "ammonified" is defined herein as meaning a material that has been treated by ammonification.

The term "preammonification" as employed herein refers to a process step that includes ammonification of nitrogen rich feedstock prior to adding to the mix feedstock that is nitrogen rich and has a high content of fermentable carbonaceous compounds including monosaccharides, oligosaccharides, starches or fermentable dietary fibers such as beta-glucans, fructans, pectins and galactans. In the process of this invention, a limit of 60 grams of monosaccharides, oligosaccharides, starches or fermentable dietary fibers per kg of VS has been determined for material that requires preammonification. Preammonification of a nitrogen rich feedstock supports ammonification of the feedstock rich in both nitrogen and fermentable carbonaceous compounds by preventing acidification of the medium.

The term "ammonia digestate" as used herein is defined as digestate originating from ammonification digester or reactor where the feedstock has been treated until preferably more than 50% of the total elemental nitrogen in the feedstock is converted to ammonia.

The term "ammonia-reduced digestate" as used herein is defined as ammonia digestate that has passed through nitrogen removal to achieve removal of at least 80% of ammonia nitrogen.

The term "mesophilic" as used herein refers to microbes able to grow and ferment in a mesophilic temperature range, and to a microbial process occurring at mesophilic temperatures, that are between 30 and 40° C. Mesophilic ammonification and methanogenesis is performed in this temperature range.

The term "thermophilic" as used herein refers to microbes able to grow and ferment in a thermophilic temperature range, and to a microbial process occurring at thermophilic temperatures that are between 45 and 60° C. Thermophilic ammonification and methanogenesis is performed in this temperature range.

The terms "methanogenic microbes" or "methanogens" as used herein refer to microbes with the ability to produce a biogas that includes methane. Methanogens are members of the phylum Euryarchaeota of the domain archaea, and belong to six orders: Methanococcales, Methanopyrales, Methanobacteriales, Methanosarcinales, Methanomicrobiales and Methanocellales. Methane production occurs along four distinct pathways: hydrogenotrophic, acetoclastic, methylotrophic and $H_2$-dependent methylotrophic methanogenesis. The members of order Methanosarcinales utilize a variety of methanogenic pathways, whereas the remaining five orders mainly perform hydrogenotrophic methanogenesis. The methanogens in methanogenic digesters have a diverse composition, with some digesters dominated by acetoclastic and some by hydrogenotrophic methanogens. Conditions such as temperature, feedstock and ammonium and acetate concentration have an effect on methanogenic community composition. Both mesophilic and thermophilic digesters have been determined to contain significant amounts of the methanogenic genera *Methanoculleus* sp., *Methanobrevibacter* sp., *Methanobacterium* sp. and *Methanosaeta* sp., whereas *Methanothermobacter* sp. was only detected in thermophilic digesters (Sundberg et al. 2013). The methanogenic community adapts to conditions within the digester, but too rapid changes can cause a total inhibition of methanogenesis. A methanogenic community is a complex network of interacting microbial species that, when starting from unfermented feedstock, slowly evolves under anaerobic conditions over a period ranging from weeks to months. Therefore, an active methanogenic community is most easily acquired as an inoculum from a working methanogenic digester.

The terms "nitrogen rich" or "nitrogen rich feedstock" as used herein refer to a feedstock with a C/N molar ratio below 15, or where the total elemental nitrogen content in volatile solids (VS) is above 40 grams N per kilogram of VS.

The terms "carbon rich" or "carbon rich feedstock" as used herein refer to a feedstock with a C/N molar ratio above 15, or where the total elemental nitrogen content in volatile solids (VS) is below 40 grams N per kilogram of VS.

The terms "total elemental nitrogen" and "total ammoniacal nitrogen" (TAN) as used herein describe alternative ways of assessing feedstock nitrogen content as well as nitrogen status during the process. These measures signify the amount of elemental nitrogen in all forms of nitrogenous compounds and the amount of nitrogen present in ammonia and/or ammonium form, respectively.

The term "nitrogen status" as used herein refers to the C/N molar ratio and/or total elemental or ammoniacal nitrogen content in a feedstock that is supplied to the process of this invention or in the contents of the vessels or digesters or reactors of the process. Nitrogen status control is achieved by running the process in such a manner that C/N molar ratio and/or total elemental or ammoniacal nitrogen content remain within optimum ranges defined herein.

The terms "means for controlling efficiency" refers generally to apparatus for regulating the process parameters. For an air stripper used for nitrogen removal, the efficiency is controlled by adjusting operational conditions including pH level, temperature and time. In an air stripper, pH and temperature can be detected by in-line sensors connected to probe controllers and further to computer software. The regulation of the process equipment is conducted by, for example, programmable logic controllers (PLCs), programmable automation controllers (PACs), remote terminal units (RTUs), and/or PC-based control systems.

The means for delivering materials throughout the process include pipes, conduits, pumpts, conveyers and the like. Solid material carriers can be, for example, chain conveyors or screw conveyors. Plumbing is, for example, fabricated from EN1.4301 AISI 304 stainless steel. Pumps are, for example, rotary lobe pumps. Gravitational arrangements are also a contemplated method for moving material."

Broadly, the process of the invention provides a measurement system for determining the total elemental nitrogen content in volatile solids or C/N molar ratio of feedstock to be fed in a first reactor, determining the amount of total ammoniacal nitrogen or total elemental nitrogen or C/N molar ratio in the ammonia-reduced digestate to be fed in a second reactor, and determining the total elemental nitrogen content or total ammoniacal nitrogen content or C/N molar ratio in reactor content of a second reactor.

The total elemental nitrogen or C/N molar ratio is determined by sensors or detectors designed to measure total elemental nitrogen and/or carbon. The sensors or detectors to measure total elemental nitrogen include dry combustion (Dumas) and wet oxidation (Kjeldahl) methods. The sensors or detectors to measure carbon include dry combustion method and, alternatively, chemical oxygen demand (COD) or total organic carbon (TOC) methods. C/N molar ratio is calculated from the detected molar nitrogen and carbon contents. Ammoniacal nitrogen is determined by sensors or detectors including enzymatic assays following fluorometric or spectrophotometric detection, ammonia-selective electrode and quick color creation methods based on Nessler's or Berthelot's method. Other sensors or detectors for monitoring and regulating the inventive process are also contemplated for detecting pH levels, the levels of specific nutrients such as sugars, starches, and fats. In particular, ammonia sensors and total elemental nitrogen sensors are contemplated. In feedstock containing proteins, protein levels are generally determined by nitrogen content, e.g., as above.

pH is determined e.g., electrochemically using pH electrode or colorimetrically using pH indicators.

Carbon containing materials are determined by art known methods. For example, sugars are determined e.g. using colorimetric or chromatographic methods. Starches are determined e.g. using a colorimetric method based on the reaction of starch with iodine or using enzymatic-colorimetric assays where starch is degraded to glucose which is then detected colorimetrically. Fats are determined using e.g. gas chromatography method, solvent extraction-gravimetric method or combined extraction-detection methods, where extraction methods include e.g. supercritical fluid extraction and detection methods include e.g. ultraviolet and flame ionization detectors."

Based on the determined nitrogen status of the feedstock or ammonia-reduced digestate or second reactor content, the process is conducted as a two-phase anaerobic digestion process, wherein the first phase is ammonification in the first reactor and the second phase biogasification in the second reactor to produce biogas. The phases are separated by a nitrogen removal step. The necessity of applying ammonification and nitrogen removal is determined by monitoring the nitrogen status of the process, i.e. when the nitrogen status allows it, the feedstock can be directly fed to the second reactor for biogasification.

The optimum C/N molar ratio of a biogas feedstock is generally considered to be between 20 and 30, i.e. 20-30 carbon atoms per each nitrogen atom. Feedstock with a C/N molar ratio below 20 would therefore be considered nitrogen rich. However, it has now been determined that in the process of this invention a feedstock with a C/N molar ratio higher than 15 can be delivered directly to the biogasification phase.

The microbial density of a biogas reactor has been determined to be approximately $1.44 \times 10^{10}$ cells/l of reactor content (Bengelsdorf et at 2012). This corresponds to an approximate dry weight of 2.5 grams of microbial biomass per liter of reactor content (calculated based on number of $5.81 \times 10^{12}$ cells per gram of dry weight as reported by Balkwill et al. 1988). Nitrogen content in dry microbial biomass is approximately 11.0% and carbon content 47.2% (calculated based on Table 1 in Fagerbakke et al. 1996). This corresponds to 0.3 grams of microbial biomass nitrogen and 1.2 grams of microbial biomass carbon per liter of reactor content, and a C/N molar ratio of 3.7. However, with certain feedstock materials optimal biogas production has now been demonstrated with reactor content C/N molar ratios between 5 and 12. These higher values are likely due to the presence of carbon that is not bioavailable and remains undigested, while still affecting C/N molar ratio value determination.

In addition to C/N molar ratio, nitrogen status control includes the determination and use of nitrogen levels in feedstock and reactor contents for process control decision making. As defined above, a carbon rich feedstock has a C/N molar ratio above 15. This C/N molar ratio corresponds to a C/N mass ratio of 12.82. Volatile solids (VS) is a measure of the organic content of a material. It is generally acknowledged that approximately 50% (mass/mass) of VS consists of carbon. Therefore, when the C/N mass ratio is 12.82, there is approximately 40 grams of nitrogen per kg of VS. It follows that in a carbon rich feedstock material there is less than 40 grams of N per kg of VS. Correspondingly, in a nitrogen rich material, the C/N molar ratio is below 15 and there is more than 40 grams of N per kg of VS.

As described above, the optimal C/N molar ratio for biogasification is 15-30. A C/N molar ratio of 30 corresponds to a C/N mass ratio of 25.64, and approximately 20 grams of nitrogen per kg of VS.

Nitrogen status determination is used as the basis for decision making in directing feedstock flow in the process of the present invention as illustrated by FIG. 1, where several routes for introducing feedstock into the system of the present invention are presented. The routes are marked in FIG. 1 with Roman numerals and are described in detail hereinbelow.

I: When the feedstock is nitrogen rich (the C/N molar ratio of the feedstock is below or there is more than 40 grams of N per kg of VS), and there is sufficient nitrogen in the biogasification reactor (the C/N molar ratio is below 12 or total ammoniacal nitrogen is above 0.1 g/L or total elemental nitrogen is above 0.3 g/L), the feedstock is directed to ammonification.

II: When nitrogen status of the carbon rich feedstock is in the optimum range for biogasification (the C/N molar ratio of the feedstock is between 15 and 30 or there is between and 40 grams of N per kg of VS), and conditions in the biogasification reactor are optimal for microbial growth and biogas production (C/N molar ratio is between 5.0 and 12 or total ammoniacal nitrogen is between 0.1 and 2.5 g/L or total elemental nitrogen is between 0.3 and 2.8 g/L), the feedstock is delivered directly to biogasification. In the contents of the biogasification reactor the C/N molar ratio is lower than in the feedstock because carbon is lost from the reactor in the form of methane and carbon dioxide. There is very little gaseous nitrogen or ammonia present in biogas, so the amount of gaseous carbon exiting the bioreactor far exceeds the amount of gaseous nitrogen exiting the bioreactor.

III: When the feedstock is nitrogen rich (the C/N molar ratio of the feedstock is below or there is more than 40 grams of N per kg of VS), but there is a state of nitrogen deprivation in the biogasification reactor (C/N molar ratio is above 12 or total ammoniacal nitrogen is below 0.1 g/L or total elemental nitrogen is below 0.3 g/L), the feedstock is directed to biogasification.

IV: When the nitrogen status of the carbon rich feedstock is not in the optimum range for biogasification (the C/N molar ratio of the feedstock is above 30 or there is less than 20 grams of N per kg of VS), and conditions in the biogasification reactor are optimal for microbial growth and biogas production (C/N molar ratio is between 5.0 and 12 or total ammoniacal nitrogen is between 0.1 and 2.5 g/L or total elemental nitrogen is between 0.3 and 2.8 g/L), or the reactor is in a state of nitrogen deprivation (C/N molar ratio is above 12 or total ammoniacal nitrogen is below 0.1 g/L or total elemental nitrogen is below 0.3 g/L), the feedstock can be either mixed with nitrogen rich feedstock for co-digestion in the biogasification reactor (IVa) or supplemented with a nitrogen source e.g. ammonia ($NH_3$) (IVb). The system of the present invention described herein includes a nitrogen removal step where nitrogen can be recovered as ammonia. This recovered ammonia can be reintroduced into the system if necessary.

Utilizing the C/N molar ratios, as described in FIG. 1, for directing feedstock flow facilitates conducting the process within the optimum range of nitrogen levels in each step of the process. The present invention simplifies operation at the feedstock interface, as compared to operation of conventional one phase and two phase anaerobic digestion processes. When control as guided by the C/N molar ratio is applied at every process step, the system can accept a variety of feedstock materials, because there is a designated route for treating each type of material.

Experiments with previously reported microbial communities, such as the mixed bacterial population S1, show that the presence of abundant carbohydrates in the feedstock leads to acidification and a decrease in culture medium pH to below 6, the activity limit of the ammonifying microbes (see e.g., Example 3 in US patent application No. 20140271438 A1). Thus, the low pH will cause ammonification to cease.

In the system of the present invention, a nitrogen rich feedstock (i.e. C/N molar ratio below 15 and >40 grams of N per kg of VS) can be directed to ammonification according to the principles discussed above and illustrated by FIG. 1. However, in the process of this invention, we have determined acidification when ammonifying nitrogen rich feedstock materials. Acidification occurs if the feedstock has a high content of fermentable carbonaceous compounds including monosaccharides, oligosaccharides, starches or fermentable dietary fibers such as beta-glucans, fructans, pectins and galactans. Acidification will not occur if the carbonaceous compounds are not fermentable i.e. comprise for example cellulosic compounds. In the process of this invention, a limit of 60 grams of monosaccharides, oligosaccharides, starches or fermentable dietary fibers per kg of VS has been determined for a material that will induce acidification. Below this limit, acidification will not occur to an extent where ammonification would be inhibited.

If a feedstock has been determined unsuitable for ammonification as a sole feedstock due to acidification, the material can be treated with help of preammonification of a nitrogen rich feedstock. Preammonification can be considered a form of sequential co-digestion. It is performed by first ammonifying a nitrogen rich feedstock that does not induce acidification. Thereafter, the feedstock that does cause acidification is mixed with the preammonified feedstock for continued ammonification. The preammonification step provides a medium with a high alkalinity and buffering capacity which mitigate acidification caused by rapid hydrolysis of the easily soluble carbonaceous compounds. In this manner, the nitrogen in the acidification causing feedstock can be mineralized as ammonia/ammonium and removed in the ammonia removal step before it could cause ammonium inhibition in the biogasification phase.

Process Setup

Figure 3:
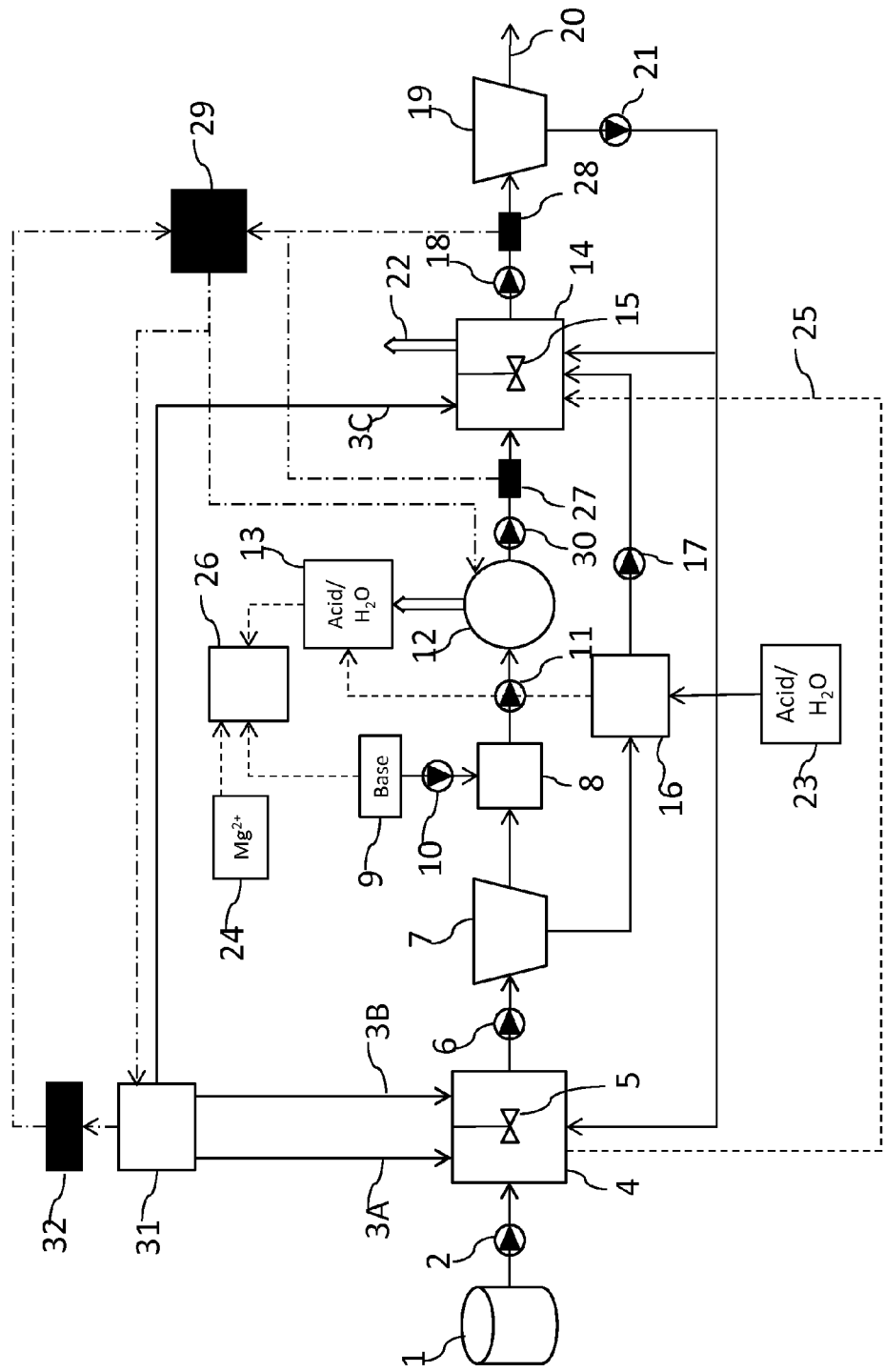
FIG. 3 is a schematic diagram of a system of the process and system of the present invention.

In FIG. 3, the reference numeral 1 refers to a vessel used for culturing the ammonifying mixed bacterial population S1. The ammonifying community can comprise another type of microbial community or a population of a single microbial species that has been deemed efficient in performing ammonification. The community, population or culture from vessel 1 is used as an inoculum in the first anaerobic digester or reactor 4 where the inoculum is delivered by means of feed pump or device 2. Alternatively, the contents of the first digester or reactor 4 can be used as inoculum for a fresh batch of feedstock. Alternatively, the inoculum need not be cultured as a part of the process of this invention, but the ammonifying community can originate from the feedstock itself (no need to add an inoculum). The inoculum can also be produced in a facility external to the process of this invention and be delivered directly therefrom to the first reactor. The amount of inoculum is at least 2.5% (volume/volume) of total reactor content volume. Alternatively, the inoculum can be present as a biofilm on solid carrier material contained within the first digester or reactor 4. Feedstock to be passed into the process is sorted on the basis of its composition, according to the scheme laid out herein with reference to FIG. 1. The sorting process is represented in FIG. 3 by feedstock sorting system 31 and conduits 3A, 3B, and 3C through which feedstock materials are delivered to digesters or reactors of the process. Feedstock sorting system 31 comprises a vessel for each feedstock to be delivered into the process and a means such as computer controlled valves for delivering the feedstock to either conduit 3A, 3B or 3C depending on nitrogen status of the feedstock and the second digester or reactor 14. Nitrogen rich feedstock is delivered to the first digester or reactor 4 via conduit 3A. Conduit 3B is used for passing nitrogen rich feedstock comprising more than 60 grams of monosaccharides, oligosaccharides, starches or fermentable dietary fibers per kg of VS to the first digester or reactor 4 after preammonification of nitrogen rich feedstock comprising less than 60 grams of monosaccharides, oligosaccharides, starches or fermentable dietary fibers per kg of VS passed to the first digester or reactor 4 via conduit 3A. Conduits 3A and 3B can optionally be replaced by a single conduit when delivery of the two types of feedstock into the digester or reactor 4 is performed sequentially. Prior to delivery to the first digester or reactor 4, feedstock can be pretreated by rendering, thermal hydrolysis, heat treatment or any other method to e.g. improve digestibility, achieve hygienisation or to extract components such as fats. During digestion, the digester contents are agitated with device 5. Agitation can be performed by any applicable manner utilizing an impeller, sparger, submersible pump or other type of device. Ammonification is performed under anaerobic conditions at mesophilic temperatures ranging from 30° C. to 40° C., or at thermophilic temperatures ranging from 45° C. to 60° C.

Ammonified material is delivered by means of feed pump or device 6 to device 7 that separates the solid and the liquid phases of the digestate. Separation of the phases can be performed by any applicable manner utilizing a decanter centrifuge, screw press, roller press, belt press or other type of device. The liquid phase is directed into equalizing tank 8 where the liquid digestate is collected for storage. If necessary, the pH of the liquid digestate can be elevated by adding base from container 9 by means of feed pump or device 10. Alkaline pH can add to ammonia stripping efficiency when removal of ammoniacal nitrogen is performed using this method. Elevation of the pH can be achieved using other methods, e.g., by removal of soluble carbon dioxide. The liquid digestate is delivered to the nitrogen removal system 12 via feed pump or device 11.

Any known nitrogen removal method can be employed. These include biological methods such as nitrification/denitrification and physicochemical methods such as precipitation, ion exchange, reverse osmosis, filtration and stripping. However, biological methods for nitrogen removal can also consume volatile fatty acids (VFA), making the material less valuable as biogas feedstock. More importantly, biological methods lead to conversion of ammonia to nitrogen gas, whereby the valuable nutrient is lost to the atmosphere. Various physicochemical methods facilitate recovery of nitrogen as pure ammonia or other compounds, typically salts such as struvite or ammonium sulfate.

Stripping is a method where a stream of air or water vapor is applied to strip pure ammonia as gas from solution. Efficient ammonia volatilization requires alkaline pH and high temperature to shift the balance of the ammonia/ammonium equilibrium towards ammonia. The gaseous ammonia is then recovered by scrubbing i.e. absorption into water to produce ammonia water or acid solution to produce an ammonium salt. When nitrogen removal is performed by air or steam stripping, the gas flow is directed into recovery vessel 13, such as a scrubber, to facilitate ammonia nitrogen recovery. Scrubbing of ammonia from the gas flow is performed by condensation of gaseous ammonia and water to form ammonia water, or absorption into water or acid solution contained within scrubber 13. The stripper/scrubber system can be employed for carbon dioxide removal to achieve elevation of pH prior to ammonia stripping. In this case, an alkaline solution is used first in scrubber 13 to absorb carbon dioxide from the liquid phase present in the nitrogen removal system 12. After carbon dioxide removal, water or acid solution is passed to scrubber 13 to achieve absorption of ammonia from the liquid phase to provide a liquid digestate stripped of ammonia.

The liquid digestate stripped of ammonia is delivered by means of feed pump or device 30 to second anaerobic digester or reactor 14 for biogasification. The second digester or reactor 14 contains a methanogenic community actively producing biogas. Carbon rich feedstock is passed to the second digester or reactor 14 via conduit 3C following principles laid out with reference to FIG. 1. In the case of nitrogen deprivation (C/N molar ratio of the second reactor content is above 12 or total elemental nitrogen or total ammoniacal nitrogen are below 0.3 or 0.1 grams per liter, respectively) in the second digester or reactor 14, nitrogen rich feedstock can be passed to second digester or reactor 14 via conduit 3C either alone, or mixed for co-digestion with carbon rich feedstock. This lowers the C/N molar ratio, or increases the total elemental nitrogen or total ammoniacal nitrogen content within the second digester or reactor 14 to optimum range (C/N molar ratio is between 5.0 and 12, or the amount of total ammoniacal nitrogen is between 0.1 and 2.5 grams per liter, or the amount of total elemental nitrogen is between 0.3 and 2.8 grams per liter). Alternatively, as described with reference to FIG. 1, ammonia derived from recovery vessel 13 can be used for nitrogen supplementation of carbon rich feedstock and passed to second digester or reactor 14 via conduit 3C, if nitrogen deprivation is imminent. Maintaining a stable, optimum range nitrogen status (as defined earlier) facilitates using a variety of feedstock materials or focusing on one specific feedstock. During digestion, the digester contents are agitated with device 15. Agitation can be performed by any applicable manner utilizing an impeller, sparger, submersible pump or other type of device. Biogasification is performed in the second digester or reactor 14 under anaerobiosis and at mesophilic temperatures ranging from 30° C. to 40° C., or at thermophilic temperatures ranging from 45° C. to 60° C.

Mesophilic biogas production is typically more stable due to higher diversity of the microbial population within the digester. It is also less sensitive to ammonia inhibition and requires less energy for temperature maintenance than thermophilic biogasification. However, thermophilic biogas production achieves shorter retention times due to higher reaction rates, and is applicable when feedstock with a stable nitrogen status is available. Temperature acclimatization can be used to turn a mesophilic biogas producing community to a thermophilic one or vice versa. This typically requires a lengthy adaptation period extending from weeks to months, so it is often preferable to acquire a new inoculum from a biogas plant operating at the desired temperature range.

Gas produced during ammonification in the first digester or reactor 4 can be directed to the second biogasification reactor or digester 14 via conduit 25 to utilize carbon dioxide and hydrogen formed during ammonification in enhancing biogas yield through hydrogenotrophic methanogenesis.

From device 7 performing separation of liquid and solid phases, solid digestate can be delivered to vessel 16 for phosphorus recovery process. In vessel 16 phosphorus-rich, e.g. bone containing waste such as slaughterhouse waste solids, can be treated with dilute inorganic or organic acid solution dispensed from container 23. The treatment is performed preferably with citric acid solution, and for a certain period of time, typically 24-48 hours at room temperature, in order to dissolve the phosphorus content as soluble phosphates. Thus, a phosphate containing liquid fertilizer component is produced, and a solid calcium fertilizer is formed as a by-product, as described in detail by U.S. Pat. No. 8,691,551 B1.

The phosphate liquid component can be also be directed to vessel 13 and used as an acidic absorber solution for ammonia gas. The ammonia product from vessel 13 can be directed to reaction vessel 26 and through further addition of magnesium containing reagent or solution from container 24, and optional addition of a base from container 9, a solid fertilizer, a struvite, can be produced. When there is little phosphorus present in the feedstock, solids can be directly delivered to the second digester or reactor 14 for biogasification. Another option is to feed the solids to the nitrogen removal process when method robustness allows treating solid matter. In this case, a liquid/solid separation step is not required before nitrogen removal, but only after biogasification. After phosphate recovery the remaining solids are delivered to second digester or reactor 14 by means of feed pump or device 17.

After biogasification in the second digester or reactor 14, the digestate is delivered by means of feed pump or device 18 to device 19 that separates solid and liquid phases of digestate. Separation of phases can be performed by any applicable manner utilizing a decanter centrifuge, screw press, roller press, belt press or other type of device. Liquid phase i.e. reject water can be recirculated by means of feed pump or device 21 to first digester or reactor 4 or second digester or reactor 14 where it serves as dilution water to achieve a desired dry matter or total solids (TS) content. Additionally, the reject water from biogasification increases ammonia concentration in the first digester or reactor 4, facilitating more efficient ammonia removal from ammonified digestate. Alternatively, reject water can be utilized as fertilizer or be directed to waste water purification. The solid fraction 20 can be utilized e.g. as fertilizer or soil improver or it can be composted. Alternatively, phosphorus rich solids can be delivered to phosphorus recovery process 16. Biogas exits from second digester or reactor 14 through gas removal conduit 22.

Finally, the setup illustrated by FIG. 3 has a first measurement system 32 for determining the carbon to nitrogen molar ratio or the total elemental nitrogen content in volatile solids in the feedstock. The second measurement system 27 determines total elemental nitrogen, total ammoniacal nitrogen or the carbon to nitrogen molar ratio in the ammonia-reduced digestate after nitrogen removal. The third measurement system 28 determines total elemental nitrogen, total ammoniacal nitrogen or carbon to nitrogen molar ratio in the second digester or reactor 14 by sampling from digestate. The setup illustrated by FIG. 3 also has a control system 29 that receives information from the first, second and third measurement system to control the efficiency of the nitrogen removal system 12 by means such as a computer controlled timer and the flow of the digestate into the second digester or reactor 14 by means such as a computer controlled valve or pump. Control is conducted based on predetermined limits for the nitrogen status within the second digester or reactor 14. The control system 29 also controls flow of the feedstock from feedstock sorting system 31 to reactor or digester 4 or 14 following principles laid out with reference to FIG. 1.

EXAMPLES

The following examples represent processes and compounds of the present invention.

While the present invention has been described with specificity in accordance with certain embodiments of the present invention, the following examples further serve only to exemplify and illustrate the present invention and are not intended to limit or restrict the effective scope of the present invention.

Example 1

Preammonification of Acidification-Inducing Feedstock Materials

The results of an experiment employing food waste (FW), porcine and bovine slaughter by-product (PB) and broiler chicken slaughter by-product (BC) are shown by TABLE 2. Food waste has a C/N molar ratio of approximately 14. It is nitrogen rich, but yet contains enough fermentable carbonaceous compounds to induce acidification and inhibit ammonification when used as a sole feedstock. Animal slaughter by-products have a C/N molar ratio below 10 and contain little carbohydrate. The results show that preammonification of a nitrogen rich material and ensuing ammonification of food waste produces highly improved yields, compared to digestion of food waste as a sole feedstock or in co-digestion with a nitrogen-rich material. Co-digestion gives a less than 20% yield when a PB 40%-FW 60% mix is used. However, when preammonification is applied, as little as 20% of PB is required for a >50% yield. The differences between feedstock materials are reflected by results with BC: it is not as efficient as PB in supporting ammonification of food waste. The beneficial effect of preammonification is, however retained. Co-digestion requires 80% BC for a ~50% yield, whereas with preammonification, 40% BC is enough for a similar yield.

TABLE 2

| Feedstock | | Yield i.e. percentage of N converted to ammonia | | | |
|---|---|---|---|---|---|
| food waste, FW (%) | (co-)digestion | SB | preammonification | SD | |
| porcine-bovine by-product, PB (%) | | | | | |
| 100 | 0 | 83.7 | 11.3 | | |
| 80 | 20 | 93.0 | 14.6 | 88.6 | 15.9 |
| 60 | 40 | 98.1 | 5.8 | 70.6 | 13.4 |
| 40 | 60 | 16.9 | 5.5 | 70.2 | 20.3 |
| 20 | 80 | 9.7 | 1.7 | 50.1 | 9.0 |
| 0 | 100 | 7.2 | 3.7 | | |
| broiler chicken by-product, BC (%) | | | | | |
| 100 | 0 | 63.3 | 16.6 | | |
| 80 | 20 | 54.9 | 12.8 | 46.4 | 8.5 |
| 60 | 40 | 17.2 | 6.3 | 48.8 | 7.3 |
| 40 | 60 | 27.3 | 8.6 | 48.3 | 10.2 |
| 20 | 80 | 20.2 | 4.2 | 24.0 | 8.8 |
| 0 | 100 | 4.9 | 3.1 | | |

Example 2

Modeling Nitrogen Content within the Biogasification Reactor

In the system of the present invention, feedstock may be sorted based on composition and selectively subjected to nitrogen removal to maintain the nitrogen concentration of a biogasification digester on an optimal level. A computational model was created for modeling the nitrogen concentration of a biogasification reactor of a biogas plant that separates carbon rich and nitrogen rich feedstocks and removes excess nitrogen either by (1) ammonification and subsequent stripping of the nitrogen rich feedstock before biogasification or (2) stripping reject water after biogasification.

The computational model calculates the nitrogen concentration of the biogasification reactor iteratively based on a set of parameters. For both feedstocks, it uses the following parameters: (1) total elemental nitrogen concentration, (2) total solids ratio, (3) volatile solids ratio and (4) proportion of total feedstock. Additionally, it uses the following parameters: (1) hydraulic retention time, (2) organic loading rate, (3) volatile solids removal ratio, (4) a constant representing how many grams of nitrogen is bound to a single gram of solids in the biogasification digester, (5) proportion of reject water in dilution water, i.e. "reject water ratio", (6) proportion of dilution water passing through stripping when stripping is performed before biogasification, (7) proportion of ammonia nitrogen that is removed by stripping, (8) proportion of total elemental nitrogen of the nitrogen rich feedstock that will be in ammonia form after ammonification and (9) which method of ammonia removal is being used.

Figure 4:
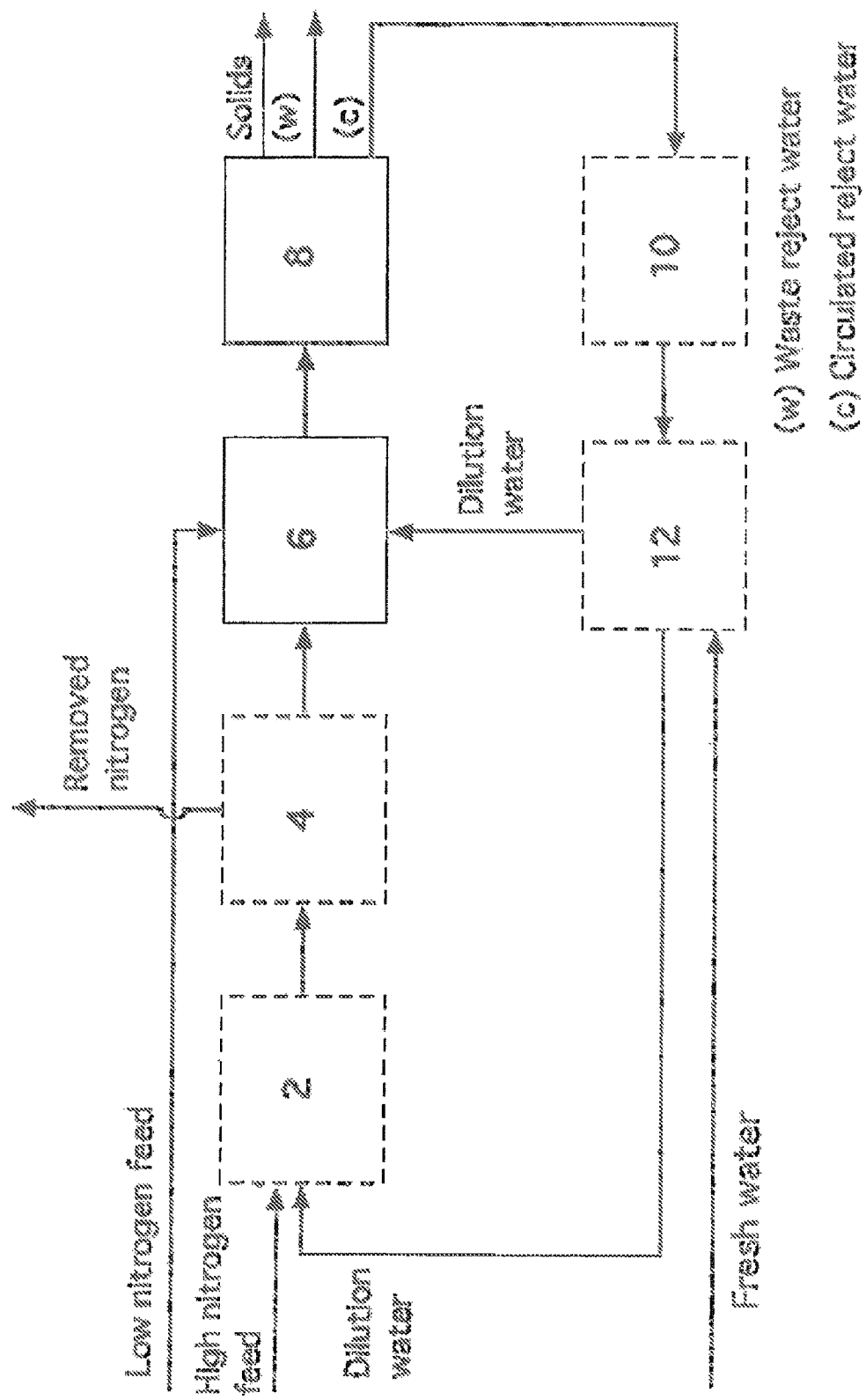
FIG. 4 is a flow chart illustrating the operation of the computer model of Example 2.

The operation of the model is illustrated in FIG. 4. In the model illustrated by FIG. 4, squares with solid lines ("-") are required processes and squares with dashed lines ("- - -") are optional process. The model assumes that the carbon rich feedstock is fed directly to the biogasification reactor 6 without any nitrogen removal. The nitrogen rich feedstock is assumed to be fed to the biogasification reactor either directly or via ammonification 2 and pre-biogasification stripping 4 steps. The ammonification step 2 is assumed to convert feedstock nitrogen to ammonia form in such a way that the resulting proportion of ammonia nitrogen of total nitrogen in the ammonified feedstock matches the relevant model parameter. The pre-biogasification stripping step 4 is assumed to remove a fixed proportion of ammonia nitrogen from the ammonia digestate.

The circulated reject water from the solids separation step 8 is assumed to have an ammonia nitrogen concentration equal to the biogasification reactor 6, as the solids are assumed to contain all of the non-ammonia nitrogen. The circulated reject water is assumed to contain no other forms of nitrogen. If stripping after biogasification is enabled in the model configuration, post-biogasification stripping 10 is assumed to remove a fixed proportion of nitrogen from the circulated reject water.

For dilution of reject water with fresh water 12, the model assumes that circulated reject water is combined with fresh water in such a way that the proportion of reject water in resulting dilution water matches the parameter "reject water ratio". Fresh water is assumed to contain no nitrogen.

The dilution water is assumed to go to the biogasification reactor 6 either directly or via ammonification 2 and pre-biogasification stripping 4. For dilution water, ammonification is assumed to have no effect, as all nitrogen is assumed to already be in ammonia form. Pre-biogasification stripping 4 of dilution water is assumed to remove a fixed proportion of ammonia nitrogen from the proportion of dilution water that goes through pre-biogasification stripping 4.

Figure 2:
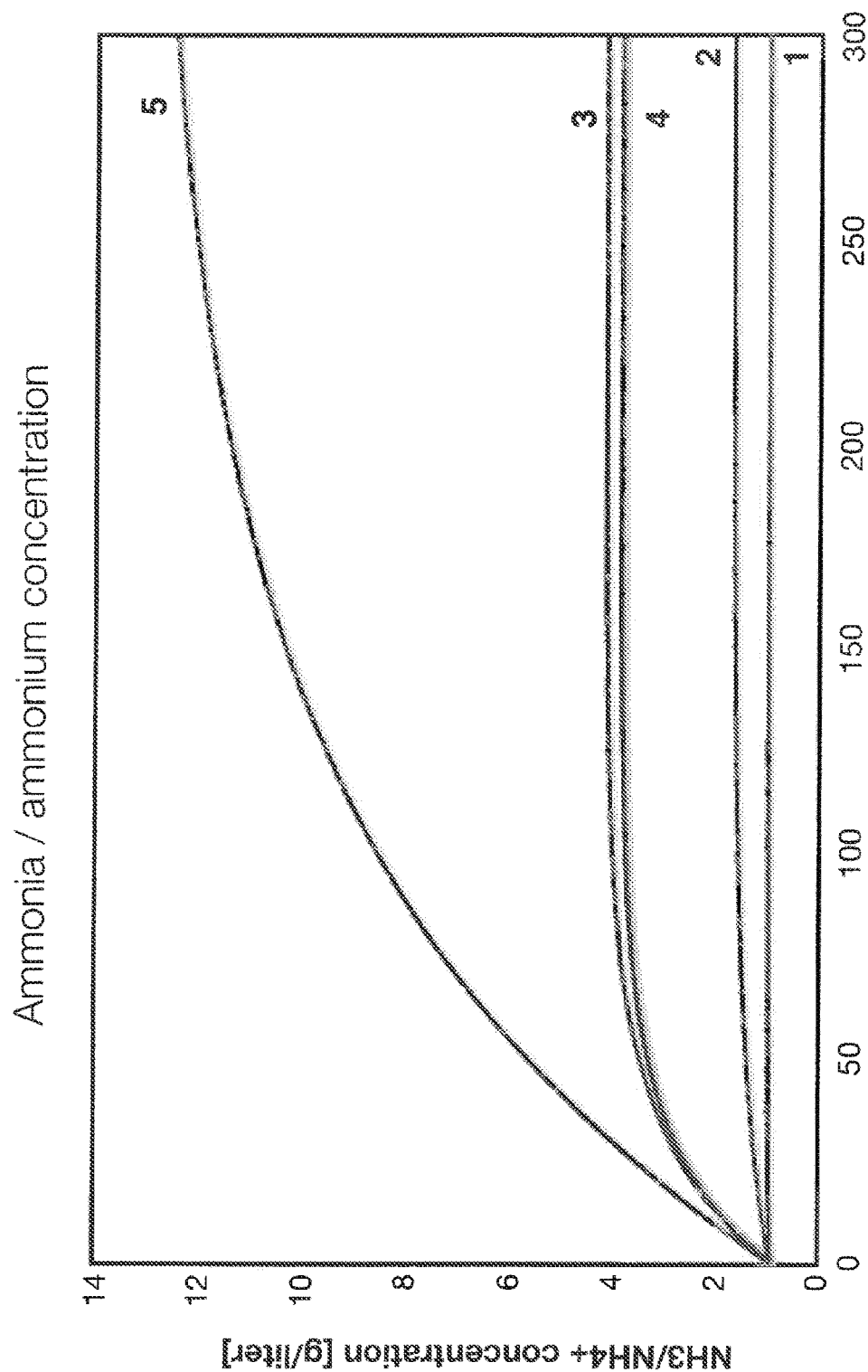
FIG. 2 is a graph showing results of a computational model of ammonia/ammonium concentration in a biogasification reactor when different nitrogen removal strategies are applied.

The model was used to estimate the nitrogen concentration of the biogasification digester of a biogas plant accepting a 50%-50% (wet mass) mix of maize silage and chicken litter as its feedstock when the plant is being run in different configurations. The configurations for each modeling run are summarized in TABLE 3, model parameters are listed in TABLE 4 and modeling results are shown in FIG. 2.

TABLE 3

| Configuration | Nitrogen removal | Reject water ratio |
|---|---|---|
| 1 | Ammonification and subsequent stripping before biogasification | 0% |
| 2 | Ammonification and subsequent stripping before biogasification | 100% |
| 3 | Stripping after biogasification | 100% |
| 4 | No nitrogen removal | 0% |
| 5 | No nitrogen removal | 100% |

TABLE 4

| Parameter | Value |
|---|---|
| Total elemental nitrogen concentration for chicken litter [g/kg] | 31.4 |
| Total elemental nitrogen concentration for maize [g/kg] | 3.2 |
| Total solids ratio for chicken litter [%] | 63.93 |
| Total solids ratio for maize [%] | 30.76 |
| Volatile solids of total solids for chicken litter [%] | 82.42 |
| Volatile solids of total solids for maize [%] | 95.66 |
| Hydraulic retention time [d] | 30 |
| Organic loading rate [kg/(m^3*d)] | 4.0 |
| Volatile solids removal ratio [%] | 80 |
| Grams of nitrogen bound to gram of solids [g/g] | 0.0286 |
| Proportion of dilution water going through ammonification and stripping before biogasification in configurations 1 and 2 [%] | 45 |
| Proportion of ammonia removed by stripping in configurations 1, 2 and 3 [%] | 90 |
| Proportion of total elemental nitrogen of the nitrogen rich feedstock that will be in ammonia form after ammonification in configurations 1 and 2 [%] | 70 |
| Initial ammonium nitrogen concentration of the biogasification digester [g/liter] | 0.9 |

The results illustrated by FIG. 2 show that for configuration 1 and 2 the ammonia nitrogen levels will, over a time of around 125 days, stabilize to a level below 2 grams/liter, which is below typical inhibition levels. For configurations 3 and 4, ammonia nitrogen levels stabilize over a similar time period, to a level between 3-4 grams/liter, which can potentially lead to inhibition. In configuration 5, ammonia nitrogen levels will quickly rise above typical inhibition levels and stabilize to a level over 12 grams per liter if operational parameters are not changed once inhibition is detected.

The results show that sorting of feedstock and subjecting nitrogen rich feedstock to nitrogen removal by means of ammonification, and subsequent stripping of the produced ammonia, allows for dilution of feedstocks with only biogasification reject water while maintaining ammonia nitrogen concentrations in the biogasification reactor below typical inhibition levels. Stripping of reject water, abstaining from using reject water for dilution and configurations with no nitrogen removal are all insufficient for maintaining a safe concentration of ammonia nitrogen in the biogasification digester.

Example 3

Nitrogen Removal by Air Stripping

Ammonia removal by air stripping is dependent on pH level and temperature. Increasing the pH is used for shifting the ammonium/ammonia equilibrium towards the free ammonia form which is easily volatilized. Ammonium ions ($NH_4^+$) exist in equilibrium with ammonia ($NH_3$) according to following reaction:

$$NH_3 + H_2O \leftrightarrow NH_4^+ + OH^-$$

Elevated temperature and aeration will increase the volatilization further and formed gaseous ammonia can be absorbed in neutral or acidic solution. In this example, an air stripper-acid scrubber column system was used for removal and recovery of ammonia.

Following the process setup described herein (see the section above in the Detailed Description entitled, "Process Setup" concerning FIG. 3), ammonified and centrifuged chicken litter broth (27.4 liters) was pH adjusted to 10.04 by adding NaOH solution (50%) from container 9. Then pH adjusted chicken litter broth was fed to ammonia removal unit by feed pump. The ammonia removal unit was in this case a pilot scale air stripper with 2.15 m packed height and an inner diameter of 16 cm. Chicken litter broth was heated to 60° C. and ammonia was transferred from liquid phase to gaseous phase with a countercurrent stream of air (liquid flow 5 L/min, air flow 75 L/min). Ammonia gas was then directed to scrubber where ammonia was trapped in a sulfuric acid solution producing ammonium sulfate as an end-product. Ammonia stripping was continued for 75 minutes, resulting in 98.4% ammonia removal. Initial and final ammonia concentrations and pH levels are presented in TABLE 5.

TABLE 5

| Feedstock material | Initial ammonia (mg/L) | pH at start | Final ammonia (mg/L) | pH at the end | Ammonia Removal % |
|---|---|---|---|---|---|
| Ammonified chicken litter | 5560.0 | 10.04 | 89.0 | 8.68 | 98.4 |

Nitrogen removal was also performed using a laboratory scale air stripper with an inner diameter of 47 mm and a total height of 75 cm. A batch of turkey feathers was ammonified (initial total solids 12%) for 14 days at 50° C., and thereafter inactivated at 95° C. for 1 h. Solids were separated by sieving and centrifugation. The air stripping/scrubbing process with fermented turkey feathers was performed following the same principle as hereinabove but using a citric acid-phosphate solution as an absorbing acid. This absorbing solution was produced by dissolving hydroxyapatite from bone by citric acid treatment according to methods presented in U.S. Pat. No. 8,691,551 B1. Stripping was performed at 43° C. for 5.5 hours with a total of 4 ml addition of 50% NaOH during stripping and a constant air flow of 25 l/min. Ammonia removal was 90.9%.

Example 4

Proof-of-Concept Demonstration in Pilot Scale

The advantages the system of the present invention (i.e. the "Ductor process") brings to biogas production were demonstrated in a pilot scale system. Two parallel biogas reactors (40 L volume) were operated under thermophilic conditions for 58 days using
A) ammonified and ammonia stripped feedstock (Ductor process) or
B) untreated feedstock (conventional process).

The methanogenic inoculum had been obtained from a biogasification digester operated at a wastewater processing plant (Viikinmäki wastewater treatment plant, Helsinki, Finland), and had been maintained by feeding wastewater sludge (OLR=1 kg VS $m^{-3}$ $d^{-1}$; HRT=20 days, temperature=50° C.) for 64 days prior to the start of the demonstration. The reactors were fed at organic loading rate (OLR) 2 kg volatile solids (VS) $m^{-3}$ $d^{-1}$ and hydraulic retention time (HRT) of 21 days. After 21 days, the OLR was elevated to 3 kg VS $m^{-3}$ $d^{-1}$ to verify process functionality at higher feedstock density. The feedstock used was a 50:50 mix (mass/mass) of chicken litter and maize silage.

Thermophilic conditions (50° C.) were used in this experiment in both reactors. However, in both ammonification and biogas production, temperatures ranging from mesophilic to thermophilic conditions, i.e. between 30 and 60° C., are feasible. In the Ductor process, the chicken litter was ammonified for 5 to 7 days at 50° C. At the beginning of ammonification, the feedstock (TS 5.2-8.4%, weight/weight) was inoculated with 2.5% (volume/volume) S1 mixed bacterial population that had been cultured using methods described in Example 1 of US patent application No. 20140271438 A1, incorporated by reference herein. Alternatively, 10% (by volume) of the preceding ammonification batch was used as the inoculum. Agitation was applied for one minute every 20 minutes by means of a submersible pump. At the end of ammonification, 63.3-83.6% of feedstock nitrogen was converted to ammonia. Separation of liquid and solid fraction was performed with a decanter centrifuge (DCE 205-00-32, GEA Westfalia, Germany). The resulting liquid and solid fractions had a total solids content of 1.5-3.3% and 26.4-29.8%, respectively.

Ammonia recovery was performed with a pilot scale air stripper as described in EXAMPLE 3 hereinabove. The ammonia stripped liquid was combined with the solid fraction in the same proportion as before decanting. To create a 50:50 feedstock mix, an amount of maize silage equivalent to the mass of chicken litter before ammonification was added. The feedstock was diluted with synthetic reject water containing the same concentration of ammonium that was present in the biogasification reactor at the same time. In the conventional process, the 50:50 mix (mass/mass) of chicken litter and maize silage was diluted with synthetic reject water as described hereinabove. The material was then fed directly to the biogasification reactor.

As seen from the results reported in TABLE 6, the initial status of the reactors was quite similar in relation to ammonium concentration and methane production. Between days and 25, the biogas reactors run with the conventional process showed somewhat higher methane production than the Ductor process reactors. After day 26, the effect of ammonium inhibition was evident in the conventional process, causing by day 51 a gradual decrease of methane production to below 60% of the amount of methane produced in the Ductor process.

Ammonium concentration remained rather constant (between 0.5 and 0.75 g $L^{-1}$) in the Ductor process throughout the run. In the conventional process, an increase from approximately 1 to 4.2 g $L^{-1}$ was observed, ammonium inhibition becoming evident when the concentration arose to above 1.5 g $L^{-1}$.

The feedstock materials used, chicken litter and maize silage had C/N molar ratios of 10.4 and 55, respectively. Therefore, they were fed to the process along routes I and II described hereinabove and as illustrated by FIG. 1.

A comparison of the Ductor process and the conventional process was also performed using actual, nonsynthetic reject water from the biogasification reactor as feedstock diluent. In this experiment, feedstock consisted only of chicken litter. The results were similar: during the 30 day run, ammonium concentration remained below 1 g $L^{-1}$ in the Ductor process while increasing from 1.6 to 3.9 g $L^{-1}$ in the conventional process. In this experiment, when the C/N of the ammonified and stripped feedstock dropped to below 15, an increase in the biogas reactor ammonium concentration was detected. This means that in addition to using different routes for directing the feedstock flux in the process, the efficiency of the ammonification and nitrogen removal system can be used to control total ammoniacal nitrogen level in the biogas reactor. In addition, the result indicates that feedstock with a C/N molar ratio below 15 must be treated by ammonification and nitrogen removal.

When studying ammonification of numerous feedstock materials, we have determined that acidification was the cause of unsuccessful ammonification of nitrogen rich feedstock materials with more than 60 grams of monosaccharides, oligosaccharides, starches or fermentable dietary fibers per kg of VS. A nitrogen rich feedstock with less than 60 grams of monosaccharides, oligosaccharides, starches or fermentable dietary fibers per kg of VS can be fed directly to ammonification. If the feedstock does induce acidification, a preammonification step with a nitrogen rich feedstock is required before adding the acidifying feedstock to the ammonification reactor.

During the pilot scale demonstration, methane was produced most efficiently at ammonium concentrations below 1.5 grams per liter of reactor content. To take into consideration the effect of using alternative feedstock materials and variations in biogas reactor microbial community, an ammonium concentration range of 0.1-3 grams per liter was determined to result in optimal methane production. This corresponds approximately to total ammoniacal nitrogen concentration of 0.1-2.5 grams per liter. As explained hereinabove, the total elemental nitrogen concentration must be at least 0.3 grams per liter to support growth of the microbial community in the biogas reactor. Consequentially, the maximum allowed concentration for total elemental nitrogen is 2.8 grams per liter to account for the proportion of ammonium nitrogen as well as the nitrogen requirement of the microbial community.

TABLE 6

Ductor process vs. conventional biogas process. Both processes were run for 58 days in 40 liter bioreactors using a 50:50 mix (mass/mass) of chicken litter and maize silage as feedstock. Results are reported as means of two parallel reactors. Variation between the two reactors was typically below 10% and in some rare instances between 10 and 15%.

| Days from beginning | OLR [kg VS m$^{-3}$ d$^{-1}$] | Ammonium concentration [mg L$^{-1}$] | | Relative methane production [%] | |
|---|---|---|---|---|---|
| | | Ductor process | Conventional process | Ductor process | Conventional process |
| 2 | 2 | 752 | 1014 | 100 | 95 |
| 7 | 2 | 718 | 1075 | 100 | 109 |
| 14 | 2 | 731 | 1204 | 100 | 112 |
| 23 | 3 | 543 | 1502 | 100 | 111 |
| 28 | 3 | 504 | 1676 | 100 | 85 |
| 37 | 3 | 655 | 2183 | 100 | 79 |
| 44 | 3 | 677 | 2728 | 100 | 79 |
| 51 | 3 | 729 | 3343 | 100 | 57 |
| 58 | 3 | 679 | 4216 | 100 | 57 |

INCORPORATION BY REFERENCE

Numerous references are cited herein, all of which are incorporated by reference herein in their entireties.

CLAIM OF BENEFIT

This application claims the benefit of U.S. Provisional Application Ser. No. 61/973,577, filed on Apr. 1, 2014, the contents of which are incorporated herein by reference in their entirety.

DEPOSIT STATEMENT

Cultures of the following biological material(s) have been deposited with the following international depository:

Centraalbureau voor Schimmelcultures (CBS)

Uppsalalaan 8

3584 CT Utrecht

The Netherlands under conditions that satisfy the requirements of the Budapest Treaty on the International Recognition of the Deposit of Microorganisms for the Purposes of Patent Procedure.

International Depository Accession

| Mixed Bacterial Population Deposited | CBS Accession No. | Date of Deposit |
|---|---|---|
| S1 | CBS 136063 | Aug. 22, 2013 |

REFERENCES CITED

Patent Documents

| US | 4,022,665 | May 1977 | Ghosh et al. |
|---|---|---|---|
| US | 6,716,351 B2 | April 2004 | Fassbender |
| EP | 1,181,252 B1 | April 2004 | Bakke et al. |
| EP | 1,320,388 B1 | November 2005 | Bonde & Pedersen |
| EP | 0,970,922 B1 | September 2007 | Moro et al. |
| US | 7,309,435 B2 | December 2007 | Rozich |
| EP | 2,220,004 B1 | September 2012 | Gerritsen & Blankenborg |
| US | 8,613,894 B2 | December 2013 | Zhao et al. |
| US | 8,642,304 B2 | February 2014 | Raap et al. |
| US | 8,691,551 B1 | April 2014 | Lahtinen et al. |
| EP | 2,039,775 A2 | March 2009* | Iwai et al. |
| WO | 2013038216 A1 | March 2013* | Kovács et al. |
| EP | 2,578,558 A1 | April 2013* | Natta & Donati |
| EP | 2,614,890 A1 | July 2013* | Wennergren & Christensen |
| US | 20140271438 A1 | September 2014* | Oksanen et al. |

*Publication date

OTHER PUBLICATIONS

Balkwill, D. L., Leach, F. R., Wilson, J. T., McNabb, J. F., White, D. C. 1988. Equivalence of microbial biomass measures based on membrane lipid and cell wall components, adenosine triphosphate, and direct counts in subsurface aquifer sediments. *Microbial Ecology* 16: 73-84.

Bengelsdorf F. R., Gerischer, U., Langer, S., Zak, M., Kazda, M. 2012. Stability of a biogas-producing bacterial, archaeal and fungal community degrading food residues. *FEMS Microbiology Ecology* 84: 201-12.

Dowd, S. E., Wolcott, R. D., Sun, Y., McKeehan, T., Smith, E., Rhoads, D. 2008. Polymicrobial nature of chronic diabetic foot ulcer biofilm infections determined using bacterial tag encoded FLX amplicon pyrosequencing (bTEFAP). *PLoS ONE* 3(10): e3326.

Fagerbakke, K. M., Heldal, M., Norland, S. 1996. Content of carbon, nitrogen, oxygen, sulfur and phosphorus in native aquatic and cultured bacteria. *Aquatic microbial ecology* 10: 15-27.

Flythe M., Russell, J. 2006. Fermentation acids inhibit amino acid deamination by *Clostridium sporogenes* MD1 via a mechanism involving a decline in intracellular glutamate rather than protonmotive force. *Microbiology* 152: 2619-24.

Ramsay, I., Pullammanappallil, P. 2001. Protein degradation during anaerobic wastewater treatment: derivation of stoichiometry. Biodegradation 12: 247-57.

Resch, C., Wörl, A., Waltenberger, R., Braun, R., Kirchmayr, R. 2011. Enhancement options for the utilization of nitrogen rich animal by-products in anaerobic digestion. *Bioresource Technology* 102: 2503-10.

Sundberg, C., Al-Soud, W. A., Larsson, M., Alm, E., Yekta, S. S., Svensson, B. H., Sorensen, S. J., Karlsson, A. 2013. 454 pyrosequencing analyses of bacterial and archaeal richness in 21 full-scale biogas digesters. *FEMS Microbiol. Ecol.* 85: 612-626.

Wolcott, R, Gontcharova, V., Sun, Y., Dowd, S. E. 2009. Evaluation of the bacterial diversity among and within individual venous leg ulcers using bacterial tag-encoded FLX and Titanium amplicon pyrosequencing and metagenomic approaches. *BMC Microbiology* 9: 226.

Zhang, C., Yuan, Q., Lu, Y. 2014. Inhibitory effects of ammonia on methanogen mcrA transcripts in anaerobic digester sludge. *FEMS Microbiology Ecology* 87: 368-77.

What is claimed is:

1. A system for optimizing production of biogas from a feedstock, which system comprises: a first reactor for treating nitrogen rich feedstock to carry out ammonification to generate an ammonia digestate;
   a system for nitrogen removal to generate an ammonia-reduced digestate from ammonia digestate;
   a second reactor for producing biogas from the ammonia-reduced digestate and/or from a nitrogen rich feedstock and/or from a carbon rich feedstock;
   means for storing each type of feedstock;
   a feedstock sorting system including a control system for directing flow of each type of feedstock to the system;
   means for delivering at least the nitrogen rich feedstock to the first reactor;
   means for delivering the ammonia digestate from the first reactor to the system for nitrogen removal;
   means for delivering the ammonia-reduced digestate from the system for nitrogen removal to the second reactor, and means for delivering the carbon rich feedstock and/or the nitrogen rich feedstock directly from the storing means and/or ammonia nitrogen from the system for nitrogen removal to the second reactor.

2. The system of claim 1, wherein the feedstock material is nitrogen rich when the C/N molar ratio of the feedstock material is below 15, or the total elemental nitrogen content in VS of the feedstock material is above 40 grams N per kilogram VS, and
wherein the feedstock material is carbon rich when the C/N molar ratio of the feedstock material is above 15, or the total elemental nitrogen content in volatile solids of the feedstock material is below 40 grams N per kilogram of VS.

3. The system of claim 1, wherein nitrogen status in the process is controlled by:
   a first measurement system determining the total elemental nitrogen content in volatile solids or carbon to nitrogen molar ratio in feedstock; and/or
   a second measurement system determining the amount of total ammoniacal nitrogen, total elemental nitrogen or C/N molar ratio in the ammonia-reduced digestate after nitrogen removal; and/or
   a third measurement system determining the amount of total ammoniacal nitrogen, total elemental nitrogen or C/N molar ratio in the contents of the second reactor.

4. The system of claim 3, wherein the system further comprises means for controlling efficiency of the nitrogen removal system and flow of the ammonia-reduced digestate stream into the second reactor, based on the measurement data from the second and third measurement system, for maintaining the amount of total ammoniacal nitrogen, total elemental nitrogen or C/N molar ratio in the second reactor within optimal range.

5. The system of claim 3, wherein the system further comprises means for controlling delivery of nitrogen rich feedstock, carbon rich feedstock or nitrogen rich feedstock comprising more than 60 grams of monosaccharides, oligosaccharides, starches or fermentable dietary fibers per kg of volatile solids into first or second reactor, for maintaining the amount of total ammoniacal nitrogen, total elemental nitrogen or C/N molar ratio in the second reactor within optimal range.

6. The system of claim 3 wherein nitrogen status in the contents of the second reactor is optimal when the C/N molar ratio is between 5.0 and 12 or the amount of total ammoniacal nitrogen is between 0.1 and 2.5 grams per liter or the amount of total elemental nitrogen is between 0.3 and 2.8 grams per liter.

7. The system of claim 3, wherein the feedstock material is nitrogen rich when the C/N molar ratio of the feedstock material is below 15, or the total elemental nitrogen content in VS of the feedstock material is above 40 grams N per kilogram VS; and wherein the feedstock material is carbon rich when the C/N molar ratio of the feedstock material is above 15, or the total elemental nitrogen content in volatile solids of the feedstock material is below 40 grams N per kilogram of VS.

8. The system of claim 5 wherein nitrogen status in the contents of the second reactor is optimal when the C/N molar ratio is between 5.0 and 12 or the amount of total ammoniacal nitrogen is between 0.1 and 2.5 grams per liter or the amount of total elemental nitrogen is between 0.3 and 2.8 grams per liter.

* * * * *